US 6,690,173 B2

(12) United States Patent
Blades

(10) Patent No.: US 6,690,173 B2
(45) Date of Patent: Feb. 10, 2004

(54) CIRCUIT AND METHOD FOR MEASURING THE CONDUCTIVITY OF AN AQUEOUS SAMPLE

(75) Inventor: Frederick K. Blades, Boulder, CO (US)

(73) Assignee: Anatel Corporation, Boulder, CO (US)

( * ) Notice: Subject to any disclaimer, the term of this patent is extended or adjusted under 35 U.S.C. 154(b) by 0 days.

(21) Appl. No.: 10/187,021

(22) Filed: Jul. 2, 2002

(65) Prior Publication Data

US 2003/0040122 A1 Feb. 27, 2003

Related U.S. Application Data

(62) Division of application No. 09/655,854, filed on Sep. 6, 2000, now Pat. No. 6,451,613.

(51) Int. Cl.[7] .................. G01N 27/02; G01R 27/22; H03F 3/45
(52) U.S. Cl. .................. 324/439; 324/693; 330/258
(58) Field of Search .................. 324/439, 693, 324/691, 722, 442, 705; 330/258

(56) References Cited

U.S. PATENT DOCUMENTS

| 3,906,353 A | * | 9/1975 | Murdock ............... 324/442 |
| 4,193,872 A | * | 3/1980 | Parkinson .............. 210/143 |
| 4,383,221 A | * | 5/1983 | Morey et al. ........... 324/439 |
| 4,432,250 A | * | 2/1984 | Albrecht et al. ........ 73/864.34 |
| 4,626,413 A | | 12/1986 | Blades et al. |
| 4,666,860 A | | 5/1987 | Blades et al. |
| 4,683,435 A | | 7/1987 | Blades |
| 4,808,930 A | * | 2/1989 | Kaiser ................. 324/442 |
| 4,825,168 A | * | 4/1989 | Igawa et al. ........... 324/439 |
| 4,868,127 A | | 9/1989 | Blades et al. |
| 5,047,212 A | | 9/1991 | Blades et al. |
| 5,132,094 A | | 7/1992 | Godec et al. |
| 5,260,663 A | | 11/1993 | Blades |
| 5,272,091 A | | 12/1993 | Egozy et al. |
| 5,275,957 A | | 1/1994 | Blades et al. |
| 5,334,940 A | * | 8/1994 | Blades ................. 324/442 |
| 5,518,608 A | | 5/1996 | Chubachi |
| 5,677,190 A | | 10/1997 | Melanson et al. |
| 5,907,108 A | | 5/1999 | García-Rubio et al. |
| 6,270,680 B1 | * | 8/2001 | Silveri et al. .......... 210/746 |

OTHER PUBLICATIONS

Donovan et al, "Evaluation of On–Line TOC Analyzers for Monitoring Recycled Water in Semiconductor Processing—Part I", *Ultrapure Water*, 2/99, p. 28–34.
Donovan et al,"Part 2: Results from the Evaluation of On–Line TOC Analyzers", *Ultrapure Water*, 3/99, p. 39–48.

* cited by examiner

*Primary Examiner*—Anjan K. Deb
(74) *Attorney, Agent, or Firm*—Michael deAngeli

(57) ABSTRACT

A circuit and method for measuring the conductivity of an aqueous sample, as used in an improved instrument for measuring the total organic carbon content of water, provides substantially instantaneous TOC measurements that are repetitively calibrated, and provides substantially improved accuracy of results in a circuit providing improved noise rejection, allowing faster response.

24 Claims, 10 Drawing Sheets

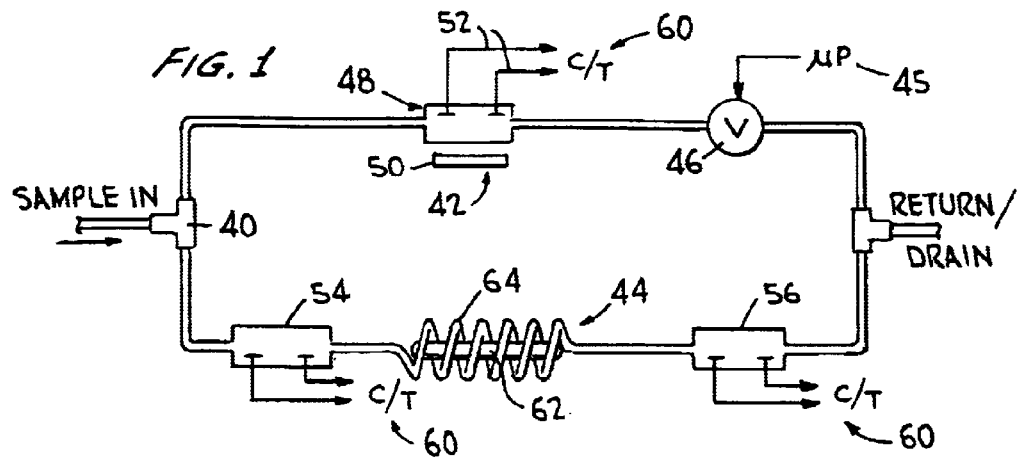
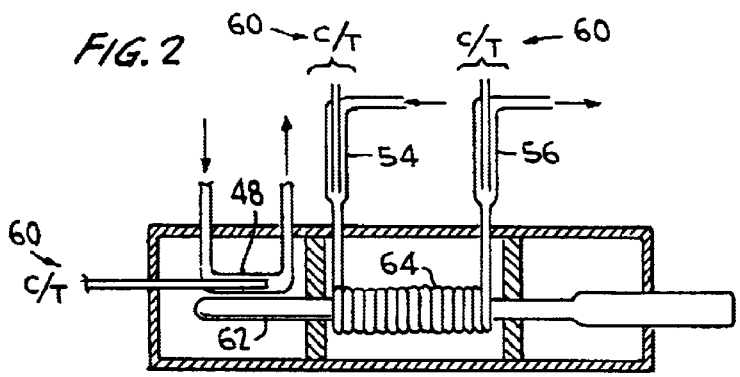
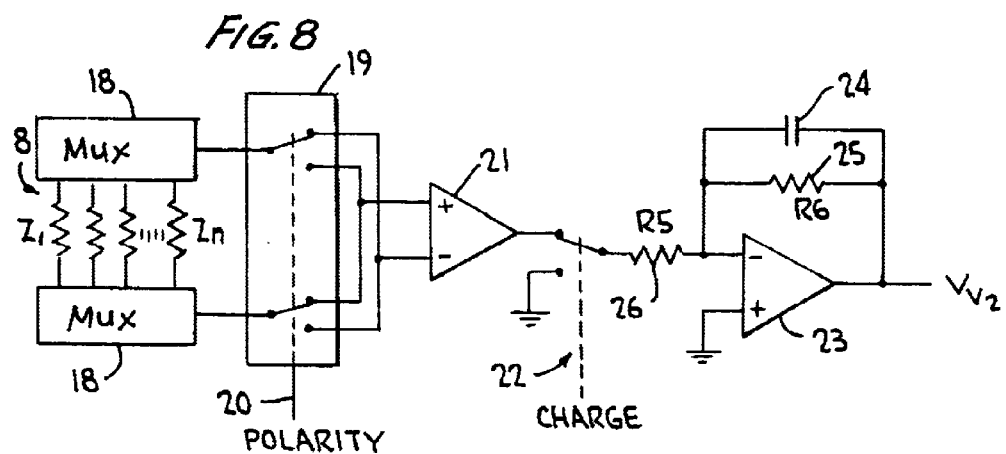

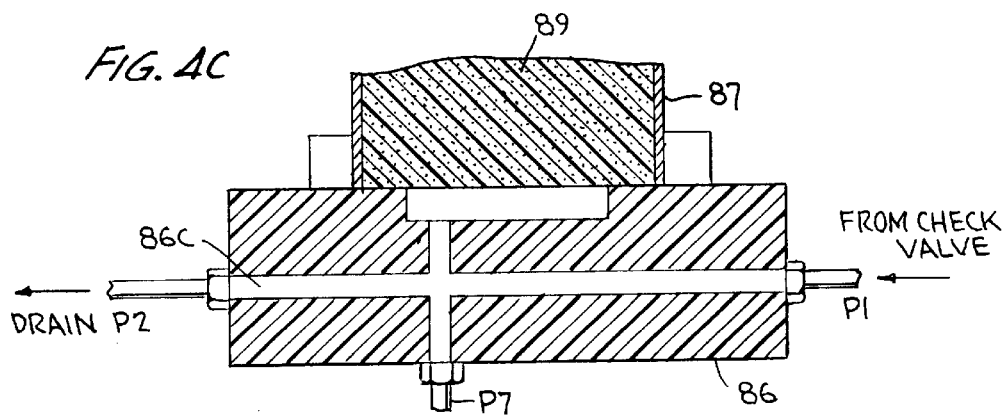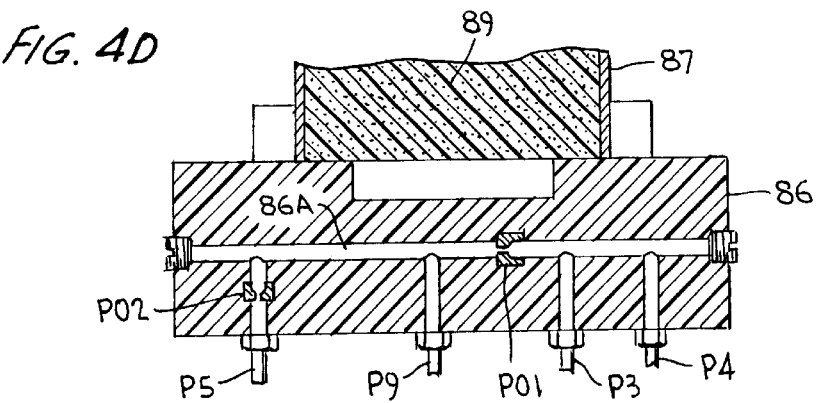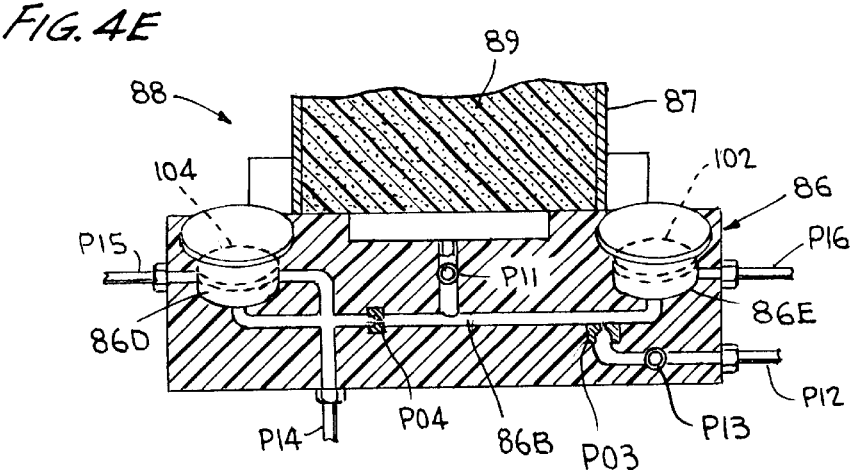

A-D RESPONSE

SYSTEM RESPONSE

INTEGRATOR RESPONSE

CIRCUIT AND METHOD FOR MEASURING THE CONDUCTIVITY OF AN AQUEOUS SAMPLE

This is a divisional application of application Ser. No. 09/655,854 filed Sep. 6, 2000, now U.S. Pat. No. 6,451,613 B1, issued Sep. 17, 2002.

FIELD OF THE INVENTION

This application relates to instruments for measuring the total organic carbon content of water. More specifically, this application discloses and claims several improvements in the instruments disclosed and claimed in the assignee's prior patents; these improvements can be used together, or, in some instances, as separate improvements.

BACKGROUND OF THE INVENTION

The assignee of the present application, Anatel Corporation of Boulder, Colo., is the assignee of a number of U.S. (and corresponding foreign) patents relating to the measurement of the total organic carbon content (TOC) of water. Monitoring the TOC of water is highly relevant in a number of important industrial processes; in particular, the semiconductor and pharmaceutical industries both use ultrapure water in large quantities.

There are several basic methodologies known to the art for measuring TOC. Most involve oxidizing organic molecules in the water, using UV radiation (see commonly assigned U.S. Pat. No. 4,626,413) possibly together with a catalyst (see commonly-assigned U.S. Pat. No. 4,868,127), and/or oxidizing reagents such as perchlorates or persulfates, to drive the reaction, and measuring the $CO_2$ thus produced. The $CO_2$ can be measured in situ, typically by measuring the change in conductivity of the water sample itself (again, see commonly-assigned U.S. Pat. Nos. 4,626,413 and 4,868,127) or can be removed therefrom. For example, it is known to remove the $CO_2$ by diffusion across a suitable membrane into a water sample of known conductivity and measure the change in conductivity of the latter; see Godec et al U.S. Pat. No. 5,132,094.

Another distinction drawn in the art is the method of determining the $CO_2$ content based on a conductivity measurement. For example, it is possible to measure the change in conductivity of a static water sample over time, i.e., monitor the conductivity as the reaction proceeds, and determine that the reaction has been completed and thus determine the final TOC value by analysis of the rate of change of the conductivity. See commonly assigned U.S. Pat. Nos. 4,626,413 and 4,666,860. This process has the advantage of providing the most accurate possible measurement. However, this "static sample" process does take some time, on the order of several minutes, for the reaction to proceed to completion (or close enough to completion that the final value can be accurately inferred; see commonly assigned U.S. Pat. No. 4,868,127 at col. 18, lines 4–32.)

An alternative method of measuring TOC is known to the art, and is referred to as the "continuous-flow" technique. In a typical implementation of this process, the conductivity of a water stream is measured before it enters a cell in which it is exposed to a UV lamp, oxidizing organics in the stream. The stream then passes into a second conductivity cell. The difference in conductivity as measured in the two cells, that is, responsive to the partial oxidation that takes place in the UV cell, is indicative of the TOC in the sample. (See, e.g., Egozy U.S. Pat. Nos. 5,272,091, Chubachi 5,518,608). Alternatively, the UV exposure and the second conductivity measurement can take place in the same cell; see commonly-assigned U.S. Pat. No. 4,868,127 at col. 22, line 40—col. 23, line 38, and U.S. Pat. No. 5,047,212 at FIG. 18 and at col. 22. However, the TOC cannot be accurately be inferred from the partial oxidation performed in such a continuous-flow process, because the change in conductivity detected thereby is a function not only of the residence time of the sample in the UV cell, but also of the rate at which the TOC is oxidized thereby. As various organics are oxidized at substantially differing rates, the change in conductivity that occurs during partial oxidation is not itself sufficient to determine the actual TOC value. Therefore the ultimate accuracy of the "continuous-flow" technique is substantially limited.

However, the continuous-flow technique does have one particular advantage, namely, that it provides a relatively rapid response. Given typical flow rates and volumes, the continuous-flow technique can provide updated measurements on the order of every 30 seconds. This allows the continuous-flow technique to be useful in monitoring ongoing processes. For example, suppose an instrument implementing the continuous-flow technique is connected in-line to a process flow, and the change in conductivity measured between the two cells.("$\Delta C$") is monitored continuously. A change in the TOC of the stream will be detected substantially instantaneously (again, in on the order of 30 seconds) as a change in $\Delta C$, and can be used to sound an alarm or the like.

It would be desirable to combine the rapid response characteristics of the continuous-flow instruments with the extreme accuracy of the static-sample instruments, and to do so is one object of the present invention.

The accuracy of the TOC measurement provided by any instrument is determined at least in part by the accuracy of the circuit used to measure the conductivity of the water sample involved, and the circuits used in the instruments sold by the assignee Anatel Corporation have evolved substantially over the last fifteen years. The original circuit is shown in U.S. Pat. No. 4,683,435; subsequent improvements are shown in U.S. Pat. No. 5,260,663 (the "'663 patent" hereinafter) and U.S. Pat. No. 5,334,940. A simplified circuit providing some of the advantages of that shown in the '663 patent is shown in U.S. Pat. No. 5,677,190 (U.S. Pat. No. 5,677,190 was originally commonly-assigned with the present application, and is referred to herein as one of the "commonly-assigned" patents.)

It is always desirable to improve such circuits, and to do so is one object of the present invention. Specifically, the response time of the instrument can be improved by increasing the intensity of the UV lamp used to drive the oxidation, but doing so increases the noise that the circuit must reject in order to function properly; it was therefore desirable to provide a more sophisticated circuit providing increased noise rejection. New components have also become available promising increased circuit performance, and to employ these to maximal advantage is another object of the present invention.

As set forth in the commonly-assigned patents mentioned above, the design of the cell in which the water sample is exposed to UV and its conductivity measured has also been refined over time. The original cell design is shown in U.S. Pat. No. 4,626,413; a first refinement is shown in U.S. Pat. Nos. 4,666,860, and 4,868,127, further refinements in U.S. Pat. No. 5,275,957, and a readily-manufacturable, relatively low-cost cell in U.S. Pat. No. 5,677,190.

It is desirable to incorporate the best features of each of these cells in an instrument that combines the advantages of the continuous-flow and static sample approaches to TOC measurement, and such is a further aspect of the invention.

Finally, as discussed in the commonly-assigned patents discussed above (all of which are incorporated herein by this reference) there are limits on the process of measuring the TOC of a water sample by oxidation of the TOC to $CO_2$, and measuring the $CO_2$ content by measuring the change in conductivity of the water sample. Specifically, the relation between TOC and resisitivity after oxidation is only linear where the conductivity of the water is sufficiently low (i.e., the resitivity is sufficiently high) that the $CO_2$ thus generated in situ is dissociated as free ions in the water, and when the TOC is below a certain level. As a practical matter this limits such instruments to measurement of TOC in ultrapure water, having conductivity of at most 0.1 microSiemens/centimeter ("$\mu$S/cm") (equivalent to resistivity of at least 10 megohm-cm); at lower purity levels, the $CO_2$ is partly dissolved and partly dissociated, necessitating a complicated compensation scheme to be employed. Similarly, typically the instruments are limited to measurement of TOC of up to 2000 ppb. It would be desirable to provide some means whereby these instruments could be used to accurately measure the $CO_2$ content of water samples of a wider range of resisitivity and TOC contents, and to provide such capability is another object of the invention.

SUMMARY OF THE INVENTION

The present divisional application is directed to improvements in circuits and methods for measuring the conductivity of an aqueous sample. More specifically, disclosed herein is an improved circuit providing improved noise rejection by using a novel differential conductivity measuring circuit in conjunction with recently-developed "sigma-delta" analog to digital converters, which provides unprecedented accuracy.

BRIEF DESCRIPTION OF THE DRAWINGS

The invention will be better understood with reference to the accompanying drawings, in which:

FIG. 1 is a schematic diagram of the instrument of the invention, combining both continuous-flow and static-sample techniques in a single instrument;

FIG. 2 shows the arrangement of the principal components of the instrument of FIG. 1 in a preferred embodiment;

FIG. 4, comprising FIGS. 4A–4E, shows a number of related views of a manifold including a pressure-regulating diaphragm used in the preferred embodiment of the invention;

FIG. 8 is a schematic diagram showing the voltage-measuring portion of the circuit;

DESCRIPTION OF THE PREFERRED EMBODIMENTS

1. Integrated Continuous-Flow and Static Sample Measurements

Figure 3A:
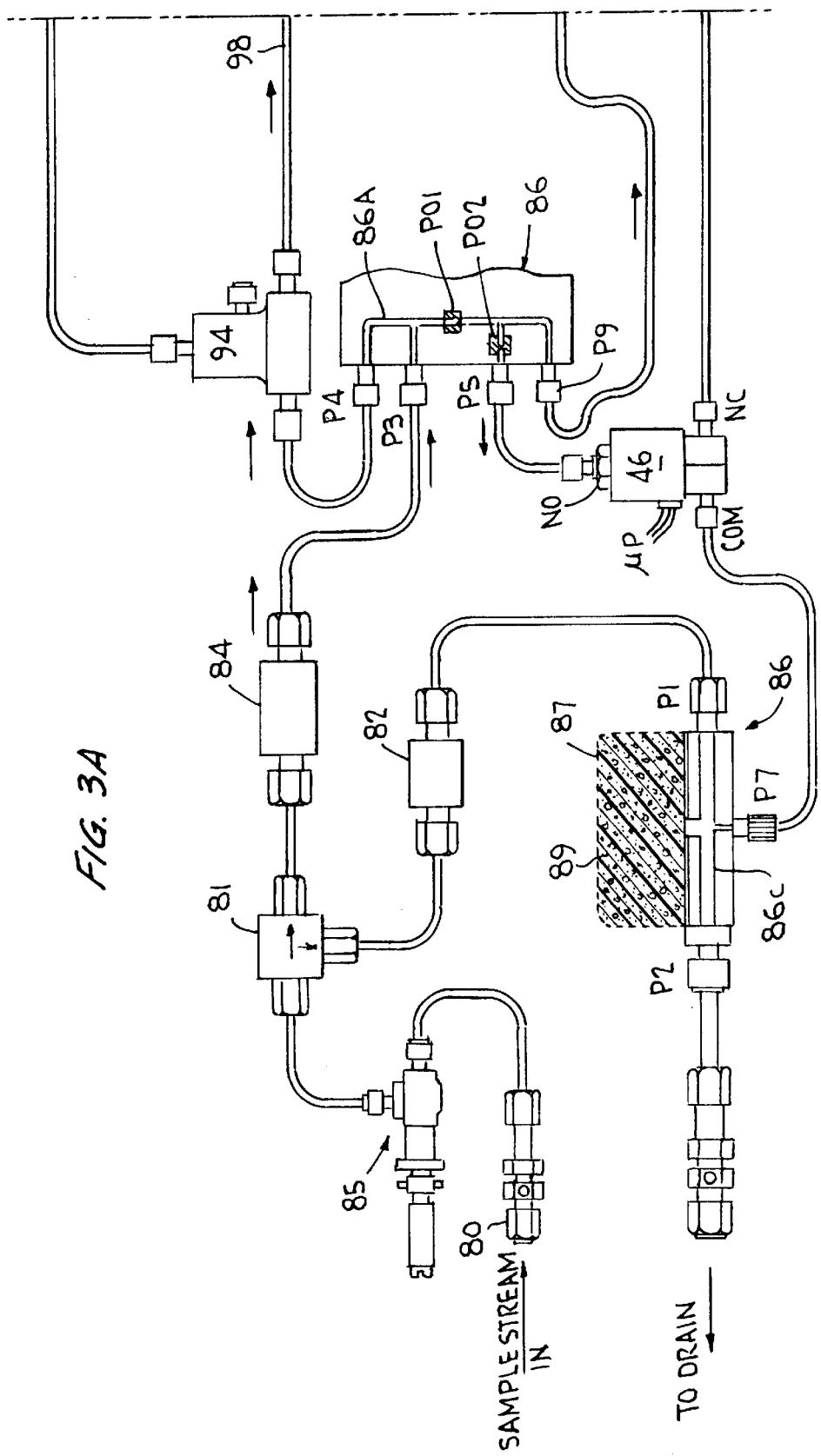
FIG. 3, comprising FIGS. 3A and 3B, provides a preferred plumbing schematic of the instrument of FIG. 1.
Figure 3B:
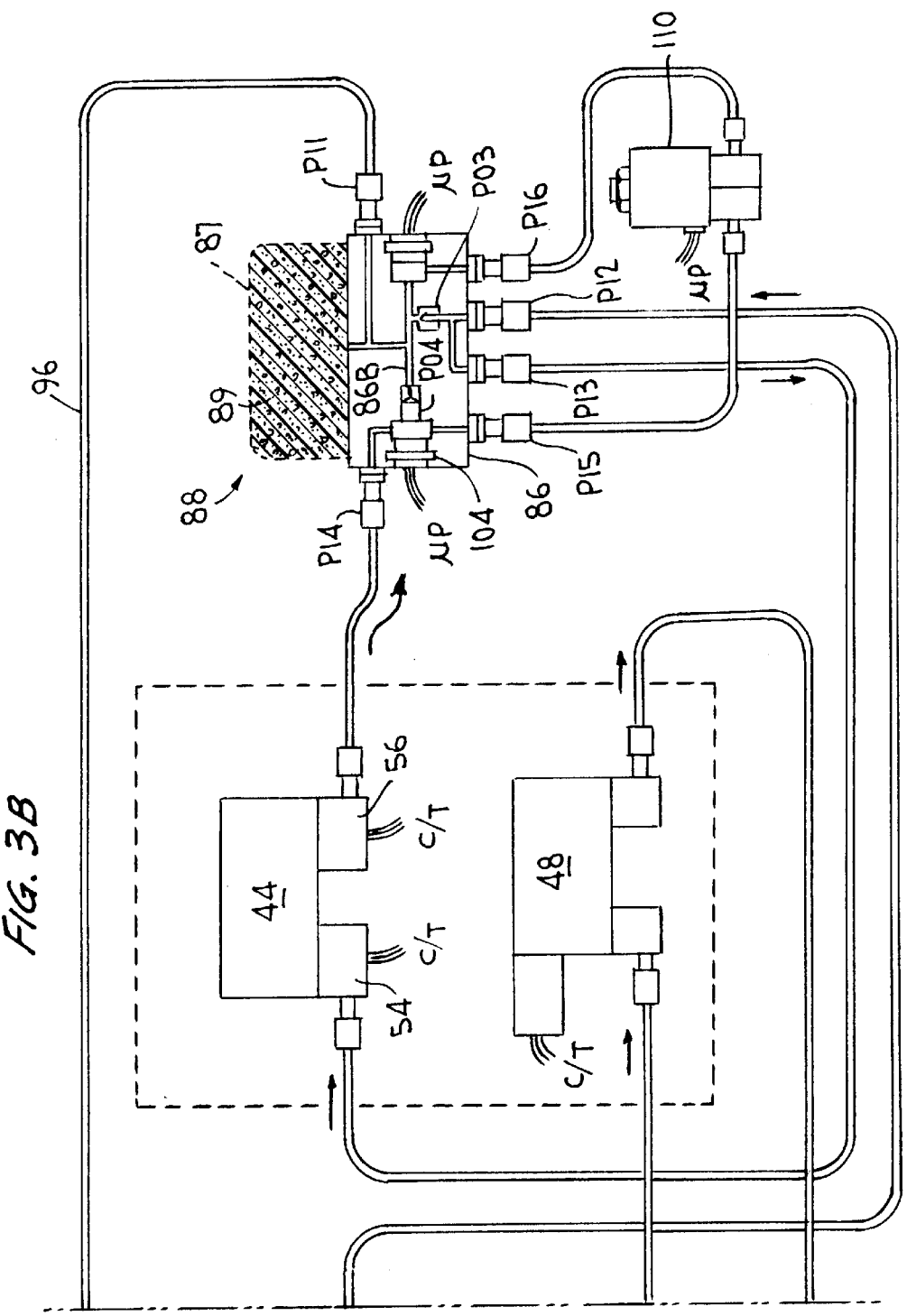

As mentioned above, one object of the present invention is to combine the advantages of the known static sample and continuous-flow processes, so as to obtain both the accuracy of the former and the rapid response of the latter. FIG. 1 shows a simplified schematic diagram of an instrument according to the invention achieving this object, and FIG. 2 shows one particularly convenient physical arrangement of the components, while FIG. 3 shows the plumbing connections therebetween in detail.

Thus, in FIG. 1, a sample stream the TOC of which is to be measured is split at a tee fitting 40, with a portion of the flow going to a "static sample side" 42 of the instrument, and another portion going to a "continuous flow module" 44. The static side 42 comprises a valve 46 controlled by a microprocessor ("$\mu$P") 45 in order to control flow into and out of a first conductivity cell 48 in juxtaposition to a UV lamp 50. Cell 48 comprises electrodes 52 connected to a circuit 60 for measuring the conductivity and temperature ("C/T") of the water in cell 48. Thus, in accordance with the teachings of the commonly-assigned patents referred to above, a water sample is admitted to the cell 48, valve 46 is closed, and oxidation begins immediately. Over the next few minutes, the conductivity varies as the organics in the cell are oxidized; the conductivity is measured as a function of time, and is analyzed to determine the completion of the reaction. (It is to be understood throughout that all conductivity measurements are accompanied by temperature measurements used in known fashion to correct the measured conductivity.) At this point the TOC of the water sample can be accurately determined, in accordance with the teachings of the commonly-assigned patents referred to above.

The continuous flow module 44 of the instrument of FIG. 1 comprises two conductivity-measuring cells 54 and 56, with a UV lamp 62 between them; alternatively, the lamp 62 can be integrated with the downstream cell 56. Cells 54 and 56 are generally similar to cell 48, and similarly comprise electrodes connected to C/T measurement circuit 60. Thus, a continuous stream of water is admitted to cell 54, where its conductivity is measured; it then flows through a UV-transparent tube 64 arranged so as to be efficiently exposed to UV radiation from UV lamp 62, so that some fraction of the TOC therein is oxidized, and into downstream cell 56, for a second conductivity measurement. The difference in conductivity ("$\Delta$C") is indicative of the amount of TOC in the water stream. However, deriving an accurate TOC value from $\Delta$C per se is difficult for reasons mentioned above, namely, because $\Delta$C depends in a complex fashion on the precise organic compounds present, the exact residence time, the intensity of the UV radiation, and other variables which are difficult to evaluate or control.

Despite the difficulty in deriving an accurate value for the TOC of a water sample using the continuous flow module, as above, it will nonetheless be appreciated that the continuous flow instrument can be usefully employed to detect sudden changes or "spikes" in the TOC content of a water stream, by connecting the instrument to an ordinary process stream, monitoring ΔC at short intervals, such as one second, and sounding an alarm if ΔC changes by more than a predetermined percentage in this period. Moreover, according to the invention, accurate values of the TOC of the stream are obtained from the static side 42 of the instrument at intervals of several minutes. These can be used in known manner to calibrate the values provided by the continuous-flow side 44. Thus, according to this aspect of the invention, the instrument provides substantially instantaneous response to changes in the TOC content of the stream being analyzed, as well as accurate, repeatable Values for TOC.

As mentioned, FIG. 2 shows a particularly advantageous arrangement of the physical components of the instrument of FIG. 1. In this embodiment, the static-side cell 48, and the upstream cell 54 and downstream cell 56 of the continuous flow module 44, are all manufactured generally in accordance with the teachings of U.S. Pat. No. 5,677,190, incorporated above. The cell design shown therein is well-proven. Specifically, this cell design provides two parallel electrodes extending out one end of an elongated sample chamber. Where the cell is to be juxtaposed to a UV lamp, as is the static-side cell 48, it is formed of UV-transparent glass; where the cells are not exposed to UV directly, as in the continuous flow module 44, they can be formed of plastic. The cell design can be readily modified as shown for convenient use in the instrument of the present invention, e.g., so that the flow exits the upstream cell 54 from one end, while the incoming flow to the downstream cell 56 is at one end, as shown. According to one aspect of the present invention, the static side cell 48 is juxtaposed to one end of UV lamp 62, while a spiral section 64 of UV-transparent tubing between upstream cell 54 and downstream cell 56 of the continuous flow module 44 is wrapped around the same lamp 62, so that a single lamp drives the oxidation on both sides of the instrument.

FIG. 3 shows, as mentioned, the "hydraulics" of the instrument, i.e., the plumbing connections required to implement the instrument of FIGS. 1 and 2. A primary goal of the design shown is to ensure that the flow rate through the continuous flow module of the instrument is constant despite permitting significant variation in the supply pressure (i.e., the pressure in the water line being monitored) and in the corresponding drain line.

More specifically, the plumbing system of the instrument of the invention was designed with several goals in mind:
1) Provide continuous flow at a constant flow rate through the continuous flow module, despite substantial variation in the pressure and flow of the associated water system. Specifically, to provide for sample flow rates of between 50 and 300 mL/min at 10–100 psi pressure.
2) Provide a source of sample flow from the associated water system to fill the static sample cell during the sampling time (consistency of flowrate not critical) with enough flow during a minimum sampling time to adequately flush the cell of the previous sample and fill it with the new sample, and do so without affecting the flow rate in the continuous flow module.
3) Allow for drain pressure from 0 psi (open to atmosphere) to 20 psi without affecting the flow rate through the continuous flow module.
4) Minimize the number of components in the sample flow stream before the oxidation cells to minimize the opportunity for contamination by the components.

The preceding design goals were achieved by designing three stages to the hydraulic system:

Stage 1: Coarse Pressure Adjustment, Primary Distribution Tee, and Stop Flow Static Cell Fill/Bypass Flow The incoming sample flow provided at 80 first flows through a user-adjusted needle valve 85, which controls the overall rate of flow of water from a stream to be monitored into the instrument of the invention. Flow from valve 85 is connected to a tee 81; one leg of tee 81 is connected to a 10 psi check valve 82 to "shave off" sample flow pressures greater than 10 psi coming to the instrument. That is, all incoming flow in excess of 10 psi is diverted to a drain connection via check valve 83, which thus serves as the coarse pressure regulator. The remainder of the incoming flow passes from tee 81 through a 50 micron filter 84 and thence to a manifold assembly 86, which comprises a single block drilled to provide several sets of connections, as detailed in FIG. 4.

Figure 4A:
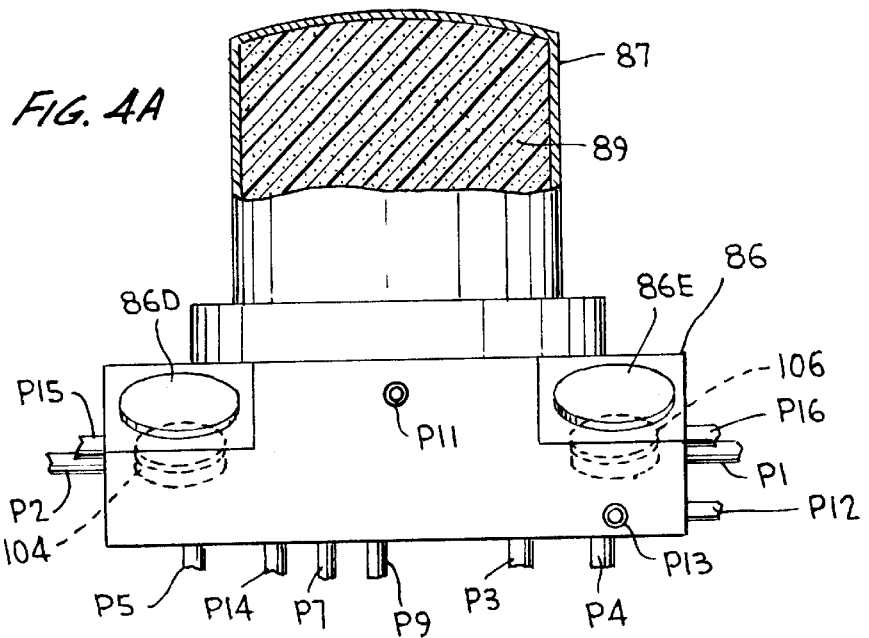
Figure 4B:
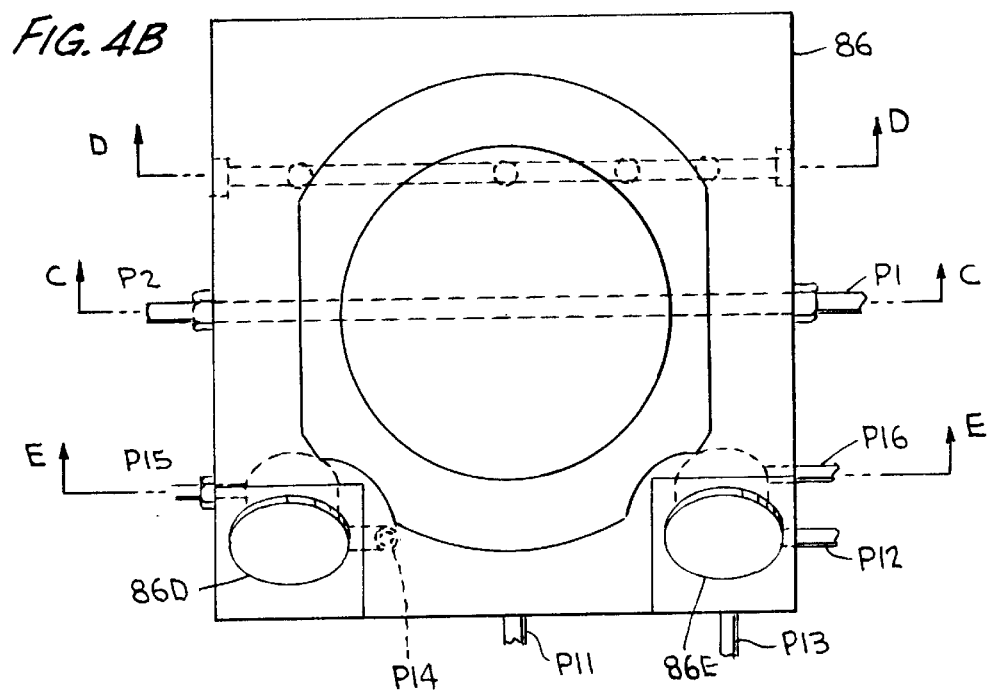

More specifically, according to the present invention a single manifold block 86 is drilled to serve as the common connecting point for a number of hydraulic lines, in total providing a single physical attachment point for three sets of lines, which, with a single exception, are hydraulically independent of one another. The three sets of lines and their connections are shown separately in FIG. 3, for ease of understanding, and the detailed structure of the manifold block 86 is shown in elevation in FIG. 4A, in plan in FIG. 4B, and in three cross-sectional views in FIGS. 4C–E, corresponding to sections taken along lines C—C, D—D and E—E of FIG. 4B, respectively. FIG. 4. Ports P1–5, 7, and 9–16 and precision orifices PO1–PO4 are commonly labeled in all views. Thus, manifold block 86 is drilled to define a "drain rail" 86C (FIG. 4C), collecting all sample flows for connection to a facility drain, a "clean flow" rail 86A (FIG. 4D), splitting the incoming flow between the static-sample cell 44 and the continuous-flow module 44, and a "differential pressure" rail 86B (FIG. 4E) providing the connections, sensors and other items needed to ensure constant flow through the continuous flow module.

More specifically, "clean flow rail" portion 86A of manifold 86 serves as a tee. The incoming sample stream at P3 is split into two flows, one going to the static sample part of the hydraulics, e.g., static cell 48, by way of P9 and one going to the continuous flow part of the hydraulics by way of P4. The latter flow flows by way of a differential pressure regulator 94 and a pressure regulation assembly 88, both discussed in detail below, to upstream and downstream cells 54 and 56. The rate of flow reaching the static sample cell 48 is limited by a precision orifice PO1 mounted in the clean flow rail 86A. (Precision orifice PO1 and three additional such orifices PO2–PO4 are sapphire orifices available from the Okeefe Company of Trumbull, Conn.; they are held in place within the respective rails in manifold block 86 by sections of tubing fitting snugly within the drilled bores defining the rails.)

The flow intended for the static sample cell 48 is controlled by an electrically actuated sample valve 46 responsive to a control signal from the microprocessor, as indicated. In the normal position of valve 46, this portion of the incoming stream flows via P5, through valve 46, and thence to "drain rail" portion 86C of manifold 86, and to the drain connection. When valve 46 is actuated, this portion of the sample stream flows via port P9 through the static sample cell 48, flushing it, until valve 46 is closed, trapping a sample in cell 48 for analysis. A second precision orifice PO2 in the line connecting clean flow rail in manifold 86A to valve 46 mimics the back-pressure of the static sample cell 48, to minimize the pressure upset when the valve 46 is opened or closed.

Stage 2: Fine Pressure/Flow Adjustment, Continuous-Flow Cell

As noted, the utility of the continuous-flow module lies in its ability to monitor the change in conductivity ΔC measured with respect to cells 54 and 56, so as to detect sudden upsets or "spikes", indicative of some sudden problem or event in the associated water purification and supply system. As further noted above, ΔC is a complicated function of the organic species making up the TOC, the residence time of the sample while being exposed to UV, and other factors. In order to reliably compare successive values of ΔC, it is essential at minimum to control the flow rate through cells 54 and 56 to be constant. This is accomplished according to the present invention as follows.

Flow to the continuous flow module 44 first passes through a precision differential pressure regulator 94, which is responsive to the drain pressure. More specifically, regulator 94 adjusts the pressure in the line 98 feeding the continuous flow system to 5 psi above the drain pressure, thus controlling the flow rate through the upstream cell 54 and downstream cell 56 constant regardless of the drain pressure. A drain pressure reference line 96 is connected to the differential pressure regulator 94 to supply the reference drain pressure.

Stage 3: Accumulator and Pressure Sensing System

In general, accumulators are hydraulic devices that collect and store fluid and energy in order to serve as system pulse dampers. In some accumulators a moving or floating diaphragm is used to store the fluid (energy) and dampen pulses. In the preferred embodiment of the present invention, the accumulator is a combination of a hydraulic manifold including rail 86B, and a chamber 87 with a Viton closed-cell foam insert 89; the Viton foam is a mechanically simpler solution than a diaphragm. As illustrated in FIG. 3 and in FIGS. 4C and E, the chamber 87 containing the Viton foam insert 89 is in fluid communication with both the differential pressure rail 86B and the drain rail 86C, such that sample exiting the continuous flow module 44 enters differential pressure rail 86B via port P14, passes through precision orifice PO4, and into chamber 87, and thence to the drain. The Viton closed-cell foam insert 89 balances the pressures from all the drain lines by compressing or relaxing as necessary to "take up" the pressure differences, by storing the energy of the pulses in the compression of the foam. The durometer and thickness of the Viton foam is selected responsive to the pressure in the system; a medium density foam with a durometer of 12 on the Shore "0" scale, with a thickness of 1.5 inches, is satisfactory in the embodiment described herein.

The pressure sensing system is comprised of two precision orifices PO4 and PO3 and two pressure sensors 104, 106 mounted in manifold block 86, which is drilled to define the passages defining differential pressure rail 86B shown in FIG. 3 and FIG. 4E. Incoming sample flow enters at port P12, passes through a tee drilling and out via port P13 to the inlet side of continuous flow module 44. Excess pressure is diverted by precision orifice PO3 to the accumulator chamber 87, i.e., so that any excess reaches the drain. Flow exiting the continuous flow module 44 passes through a chamber 86D containing first pressure sensor 104, through a precision orifice PO4, and to the accumulator chamber 87. The pressure of the flow reaching the accumulator is monitored by the second pressure sensor 106, disposed in a second chamber 86E. Pressure sensors 104, 106 comprise diaphragms the deflection of which is measured by piezoelectric elements, as is well known in the art. The magnitude of flow through the system is determined by the ratio of the diameters of the two precision orifices PO3, PO4. Stability and rate of flow is measured by the differential pressure across the second orifice PO4, i.e., by comparing the pressure as sensed by sensors 104, 106. Since the flow to drain from orifice PO4 is connected to the flow to drain from the continuous-flow cell 48 through orifice PO3, pressure is balanced between the two orifices and excess pressure/flow naturally goes through the first orifice PO3 to waste, prior to the continuous-flow cell 48, stabilizing the flow through the continuous-flow cell 48.

More specifically, orifice PO4 is the final controlling point for the constant (4 mL/min) flow through the continuous flow module. Flow through orifice PO3 to the accumulator chamber to drain is typically about 15 mL/min. This arrangement provides very constant pressure and flow through the continuous flow cell. Pressure is maintained to nominally 5 psi with a precision of +/−0.02 psi. The remainder of the flow, nominally 4 mL/min, exits the accumulator manifold via P13 and passes through the continuous flow module 44. After exiting the continuous flow module 44, flow re-enters the accumulator manifold, passes by pressure sensor 104, through precision orifice PO4, into the hydraulic line connected to pressure sensor 106 and into the accumulator chamber. The pressure drop across orifice PO4 is measured by comparing the values provided by sensors 104 and 106. A positive pressure drop indicates flow through the continuous flow module 44. This pressure drop is displayed on a screen (not shown) ultimately used to display the measured TOC, and is used by the operator to adjust needle valve 85 on installation to ensure adequate flow. As noted, the operating pressure in the continuous flow module 44 is designed to be 5 psi, which corresponds to a flow rate of approximately 4 mL/min.

It should be noted that the actual values of the flow rate and pressure are not per se important as long as they are in an appropriate range. However, the performance of the system is dependent on the stability of the flow rate through the continuous flow module. More specifically, as noted above, the degree to which TOC in the water stream is oxidized while in the continuous flow module is determined by its residence time in the continuous flow coil 64 (FIGS. 1 and 2), where the TOC is oxidized by exposure to UV light. Small changes in pressure and/or flow can result in changes in the degree to which the TOC is oxidized, which can-be misinterpreted as changes in the TOC itself. Therefore the pressure and flow through the continuous flow cell must be very stable.

By comparison, stability of the flow through the static sample cell 48 is not critical. The flow must simply be sufficient to adequately flush the cell of the previous sample and fill the cell with the current sample to be analyzed. Therefore the precision pressure/flow system is not required for the static sample side of the instrument.

Accumulator Design

Since another goal of the design is to allow constant flow through the system with a drain pressure above atmospheric pressure, it was necessary to collect all the drain lines from the system into an accumulator and provide for a pressure equalizing system. Normally accumulators accomplish this by providing a moving diaphragm with drain pressure on one side and a fixed volume of gas on the other. This was unduly complicated for the instrument of the invention, so a piece of rubber of appropriate durometer value relative to the system pressures was used in place of the diaphragm. Since the system pressure was low (5 psi) and the drain pressure was low (20 psi maximum) the durometer needed to be very low. As mentioned above, Viton rubber material was chosen for this application due to its high chemical stability. The correct durometer value was achieved by using Viton foam rubber. Closed-cell foam was chosen to avoid variation in the durometer value over time. That is, if open cell foam had been used, the cells would eventually be filled by the sample drain water, increasing the durometer and degrading the pressure equalization ability. The foam fills most of the accumulator chamber and compresses or relaxes against the drain pressure as the pressure changes. Since the Viton foam is soft it can move around in the chamber against changing pressure. To prevent the foam from moving, a post (not shown) may be provided in the center of the chamber, holding the Viton in place laterally so that it can only move as a result of compression against drain pressure. All system drain lines are connected through the accumulator manifold 86 to the accumulator chamber 87 mounted on top of the manifold. The accumulator chamber 87 is connected to the system drain through port P2, and is piped to the customer's drain. The drain pressure can be between 0 psi (atmospheric) and positive 20 psi, and the stop flow and continuous flow hydraulic systems will still provide the correct and constant flow rates required for analysis.

As noted above, according to one aspect of the invention, the value for TOC that is provided by the static sample cell 48 is used to calibrate the repetitive values provided by the continuous-flow module 46. However, the value for the conductivity of the water sample before oxidation, which is representative of its total inorganic carbon content ("TIC") is used in the calculation for TOC according to the equation TC (total carbon) TIC+TOC. That is, the conductivity value measured at the completion of the oxidation in the static sample cell is actually representative of the TC, and the TIC value must be subtracted therefrom to yield TOC, which is normally the quantity of direct interest. (TIC is normally in ionic form before oxidation and thus can be measured by evaluating the conductivity.)

The accuracy of the continuous flow TOC measurement is dependent on the accuracy of the difference ΔC between the conductivity as measured by the inlet and outlet conductivity cells of the continuous-flow module, so the inlet and the outlet cells must agree well when measuring water of the same conductivity, i.e., in the absence of oxidation. Furthermore, as the conductivity measurement made on the inlet side of the continuous-flow module is also used by the static-sample TOC measurement as the TIC measurement, the ultimate accuracy of the TOC value provided by the static sample cell is also dependent on how well the two cells agree. [It will be appreciated that the TIC measurement could also be made in the static-sample cell, i.e., before oxidation commences. However, this would necessitate turning off the lamp to which sample in the static-sample cell is exposed, so as to avoid interference. As the same lamp is desirably used to power the oxidation reaction in both the static-sample and continuous-flow cells, the lamp must be continuously energized in order to provide a series of comparable measurements from the continuous-flow module.] Therefore, from time to time it is necessary to "balance" the conductivity reading of the static sample cell and the two conductivity-measuring cells of the continuous-flow module. This is accomplished by turning off the UV lamp and putting the static sample cell in the purge mode, i.e., so that un-oxidized sample water is flowing through all three cells. The conductivity measurements provided by the static sample cell and the two conductivity cells of the continuous-flow module are adjusted, if necessary, so that they all read the same conductivity for the un-oxidized sample water.

Since the flow through the continuous-flow module is slow (4 mL/min.) there is the opportunity for a temperature gradient through the continuous-flow module 44, even with the UV lamp off, due to temperature gradients in the cell assembly. To allow for a higher flow through the continuous-flow module during calibration, an electrically actuated calibration valve 110 is provided. When valve 110 is open, flow entering the accumulator manifold from the continuous-flow module 44 through P14 exits through P15, passes through valve 110 and enters the accumulator manifold through port P16. In this way the flow by-passes the precision orifice PO4 which normally regulates the flow through the continuous-flow module 44 to 4 mL/min. In this configuration the flow is nominally at least 15 mL/min, which is more than sufficient to prevent heating of the sample water in the continuous-flow module 44 due to thermal gradients in the continuous-flow module during cell balancing. This change in flow rate in the continuous-flow module has no effect on the flowrate through the static-cell system in the purge mode.

2. Conductivity/Temperature Measurement Circuit

As indicated above, the instrument of the invention comprises three cells in which the conductivity and temperature of a water sample or stream must be measured accurately. As discussed in detail in commonly assigned U.S. Pat. Nos. 5,260,663 and 5,334,940, it is generally preferable to measure the conductivity by applying a square-wave AC signal of known amplitude (i.e., voltage) to the cell, measuring the current $I_{cell}$ through the cell, and determining the resistance from Ohm's Law, i.e., V=IR. While the improved circuit of the invention is disclosed in connection with an instrument for measurement of TOC in water samples, the circuit disclosed herein could also be used to measure the conductivity of solutions in other contexts.

A. Background

Figure 5:
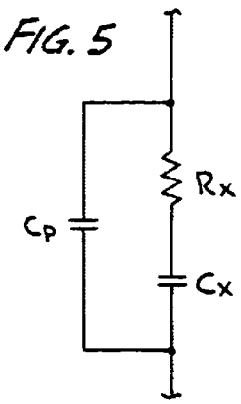
FIG. 5 shows an equivalent circuit for each measurement cell of the instrument.

Accurately measuring the resistance across a conductivity cell containing a small amount of $CO_2$ in essentially ultrapure water is not simple. As set forth in the prior patents referred to above, the '663 patent being referred to specifically, the conductivity cell can be modeled as a two-terminal "black box" having a series capacitance $C_x$ and series resistance $R_x$ in parallel with a parallel capacitance $C_p$. See FIG. 5 hereof, and FIGS. 1 and 2 of the '663 patent. More specifically, the '663 patent shows the manner in which $C_p$ can be fully charged during a first part $t_c$ of each half cycle of the square-wave drive signal, thus being fully compensated for. The '663 patent further describes the desirability of providing a low value of the feedback resistance employed during $t_c$ in order to supply sufficient charging current to rapidly charge $C_p$. The '663 patent also discloses minimization of the error due to $C_x$ by increasing the drive frequency as the conductance goes up. The '663 patent also describes the concept of synchronous rejection of lamp noise. More specifically, a major source of high-frequency noise in the instrument described in the '663 patent was the high-frequency switching power supply driving the mercury vapor lamp used to energize the oxidation of TOC in the sample. The '663 patent discloses a method for "synchronous averaging" of the output signal to reduce or eliminate noise from this source; see col. 11, lines 4–29. The instrument of the present invention has a mercury vapor lamp that is about six times as powerful as that used in the product corresponding to the '663 patent, and which produces correspondingly more noise. Better noise rejection is therefore needed. Moreover, as noted, the instrument of the present invention also comprises three cells, and so requires three sets of conductivity and temperature measurements to be made substantially simultaneously, necessitating faster measurements.

The circuit of the present invention uses a new, fully differential design that offers higher noise rejection (so much so that the lamp noise no longer needs to be eliminated by synchronous averaging), provides multiplexed input channels and faster response time.

Two embodiments of the inventive circuit are disclosed: a fixed-gain resistive version and a variable gain integrating version. Both are fully differential, multi-channel configurations that offer high common-mode noise immunity and high linearity. The fixed-gain resistive embodiment of the circuit of the invention offers a number of selectable fixed-gain ranges and uses a fixed resistor as the gain element for each range. This embodiment can be implemented and/or operated in either AC or DC mode. AC mode is preferred for, e.g., the measurement of the conductivity of electrolyte solutions such as water containing dissolved $CO_2$, as encountered in connection with the TOC instrument described herein, where a DC measurement voltage would cause migration of constituent ions and eventual polarization of the cell. DC mode is commonly used to measure the resistance of temperature-sensing elements, e.g., thermistors used to correct the conductivity measurements.

The variable-gain integrating embodiment of the circuit of the invention uses a single capacitor as the gain element for each "side" of the differential circuit to provide continuously variable gain, that is, the gain is inversely proportional to the drive frequency. This embodiment offers exceptionally high noise immunity. This embodiment can be operated in AC mode only.

In AC mode, both $C_x$ and $C_p$ are compensated for in the same manner as in the circuit of the '663 patent, that is, during a time $t_c$ of each half-cycle of the square-wave drive signal the feedback resistance is made low in order to provide sufficient current to fully charge $C_p$ before the measuring circuit is switched in. Since the gain is inversely proportional to the drive frequency by design, the error due to $C_x$ is minimized.

Although the circuits disclosed can be employed together with any desired type of analog-to-digital ("A-D") converters, both circuits are designed to take full advantage of recently-available sigma-delta A-D converters. These converters provide multiple-pole digital filtering as a part of the conversion process and are used to great advantage in the present design to filter out noise from the mercury lamp.

B. Measurement Method

In both embodiments of the circuit of the invention, the voltage across the cell ($V_{cell}$) and the current through the cell ($I_{cell}$) are measured and converted separately to digital values. The cell resistance is then calculated in the microprocessor 45 as a ratio (by comparison, in the circuit of the '663 patent, a single ratiometric A-D converter was used). The TOC content of the water sample can then be determined from the cell resistance. The reason for measuring V and I separately in the present circuit is to provide the ability to independently measure and thus compensate for both voltage and current offsets. The current offset is simply measured by taking a reading with an open circuit i.e., when $I_{cell}=0$. This offset is then subtracted from each subsequent current reading before taking the ratio. The voltage offset is comparably made by taking a voltage measurement when $V_{cell}=0$. This voltage offset is likewise subtracted from each subsequent voltage measurement before the ratio is taken.

More specifically, any type of A-D converter can be used to convert the resulting analog values to digital values, as needed for further processing by the microprocessor to yield a value for the TOC of the sample. However, the "sigma-delta" A-D converters now available, which were not available when the circuit of the '663 patent was developed, allow performance approaching 24-bit resolution (as opposed to about 18 bits in the best case with the circuit of the '663 patent). To achieve anything approaching 24-bit performance (recognizing this represents an accuracy of one part in 16 million) it is critical to compensate all such offsets.

C. Fixed-Gain Resistive Circuit i. Current Measurement

Figure 6:
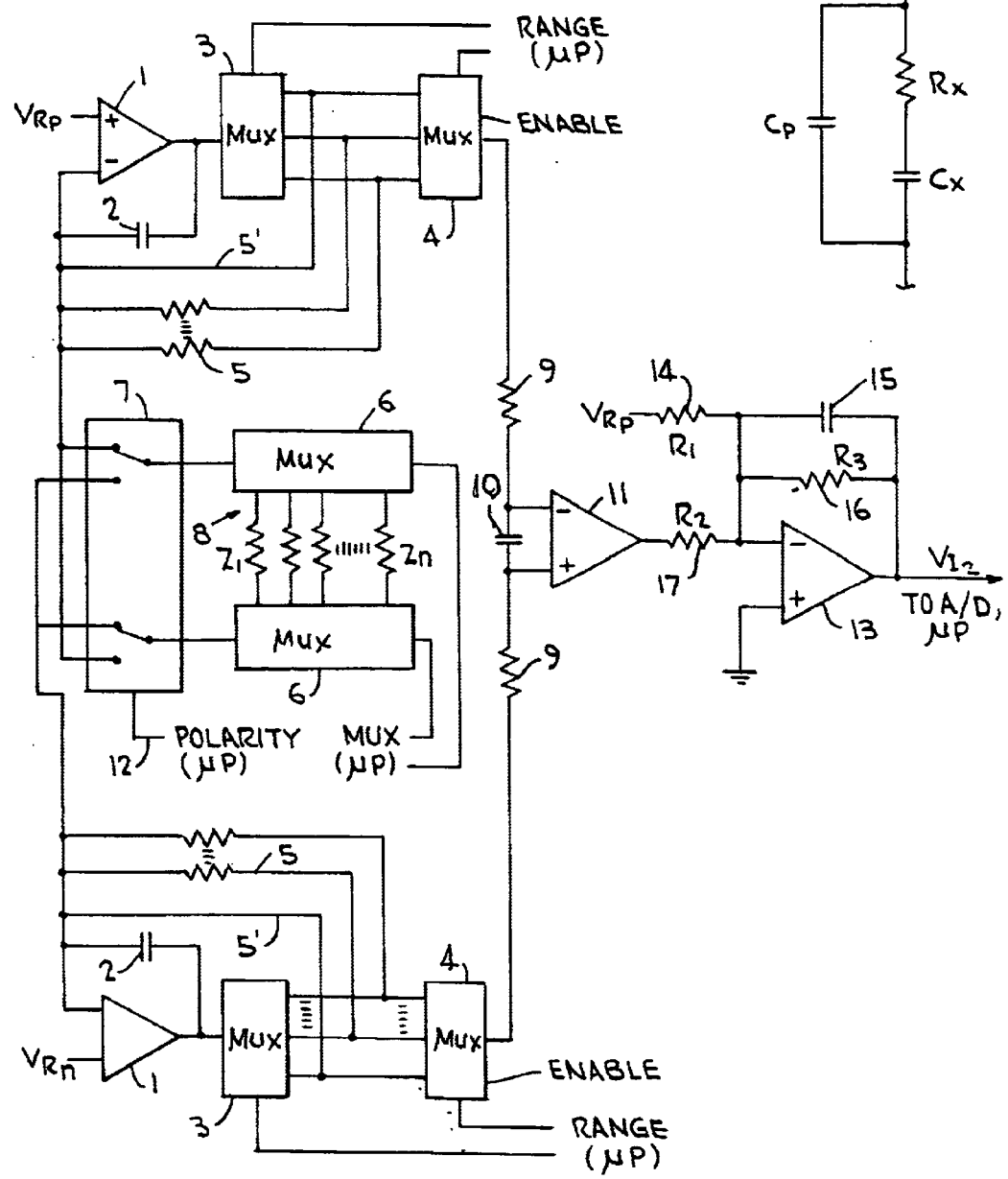
FIG. 6 shows a schematic diagram of the current-measuring portion of a fixed-gain, resistive embodiment of the preferred conductivity-measurement circuit of the invention.
Figure 7:
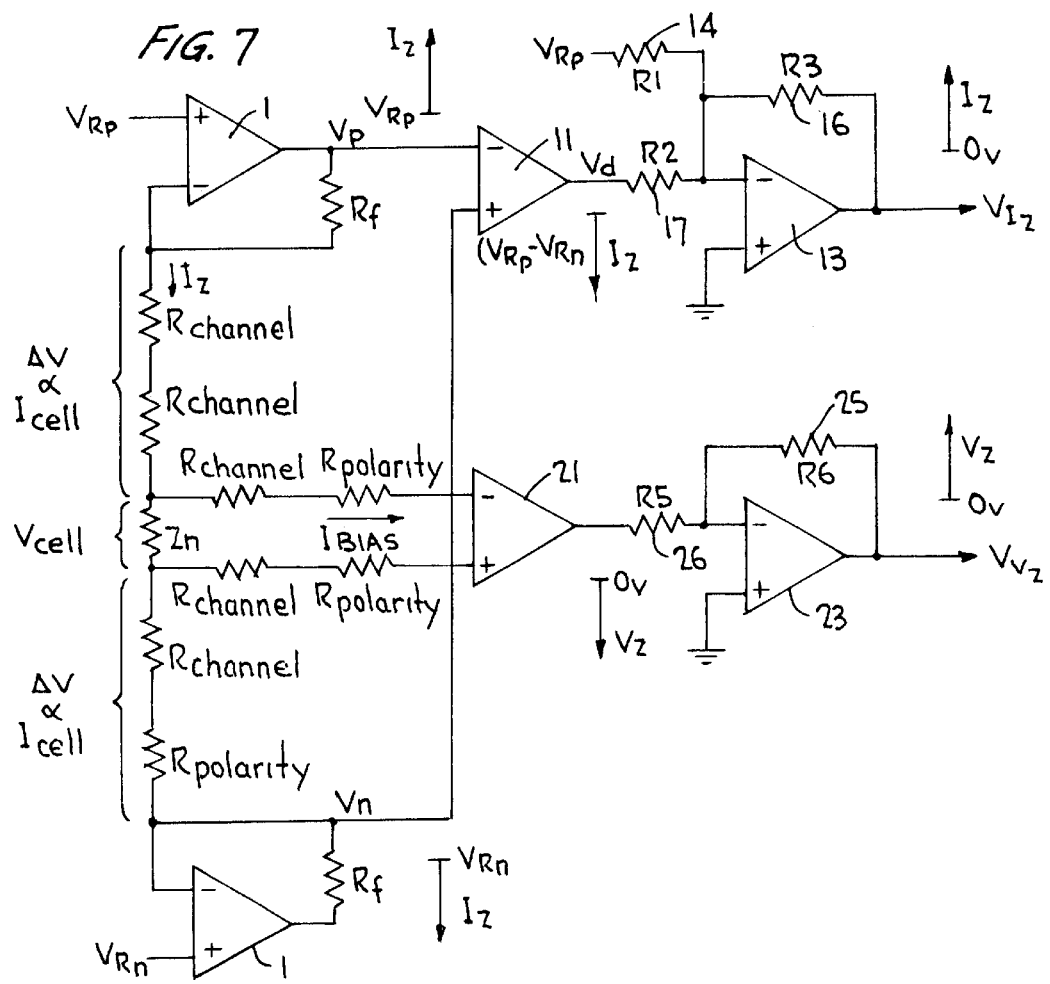
FIG. 7 is an equivalent circuit diagram corresponding to FIGS. 6 and 8.

As noted, the current-measuring portion of the circuit of the invention, in its fixed-gain resistive embodiment, is shown in FIG. 6. FIG. 8 shows the voltage-measuring portion of the circuit, which has only the multiplexed impedances to be measured in common with the portion of the circuit shown in FIG. 6. FIG. 7 shows a simplified DC equivalent circuit of both the current- and voltage-measuring circuits, shown together. It should be appreciated that the FIG. 8 voltage-measuring circuit is also used in the integrating version of the current-measuring circuit shown in FIG. 9.

Referring first to FIG. 6, the conductivity cells, thermistors measuring the temperatures in the cells, and certain reference values used to measure any offsets are shown as impedances $Z_1, Z_2, \ldots Z_n$ connected between multiplexer pairs 6. Multiplexer pairs 6 are responsive to a signal ("MUX") from the microprocessor 45 that controls operation of the overall instrument, i.e., the microprocessor determines which of the multiplexed impedances is measured at any given time. The impedances are connected to the rest of the circuit by the multiplexers 6 through a polarity-reversing DPDT switch 7, responsive to a "POLARITY" signal from the microprocessor 45. As will be apparent, the circuit is symmetrical, in that it comprises two substantially identical "sides" connected across the multiplexed impedances and a differential amplifier 11. By providing the matched sides, in full differential mode, numerous sources of noise and inaccuracy are automatically compensated for and eliminated.

As will be observed, both of the symmetrical sides of the circuit comprise op-amps 1. The inverting inputs of the op-amps 1 are connected to the impedance to be measured, e.g., across the electrodes of one of the conductivity cells of the TOC measuring instrument described herein. Op-amps 1 with their associated feedback resistors 5 thus form differential current-voltage converters. A pair of multiplexers 3 are each responsive to a "RANGE" signal from microprocessor 45 to select one of several feedback resistors 5 (i.e., both multiplexers 3 select a feedback resistor 5 of the same value, which can be a short, as indicated at 5') to determine the gain of the circuit and thereby the range. A pair of second multiplexers 4, operated to take the same channel as the corresponding first multiplexers 3, sample the voltages at the top of the corresponding selected feedback resistor 5; these voltages are fed to an instrumentation amplifier 11 through a single-pole filter provided by resistors 9 and capacitor 10. The output of the instrumentation amplifier 11 is then fed to an inverting buffer amplifier 13 for two purposes; first, to provide a summing junction to feed the offset correction current through resistor 14, and second, to add an additional pole of filtering with feedback capacitor 15. As will appear below, the two inputs thus provided to the instrumentation amplifier are opposite one another, providing superior noise rejection. The amplifier 11 should be selected for low input bias current to keep the voltage drop low across the switch resistance of multiplexer 4. Capacitors 2 are selected to stabilize the corresponding op-amps 1 during switching intervals.

The non-inverting inputs of the two current-voltage converters are held at reference voltages $V_{Rp}$ and $V_{Rn}$, typically +0.5 volts and −0.5 volts respectively. The feedback loops comprising resistors 5 maintain this same voltage difference at the inverting inputs and hence across the cell (noting that switches 6 and 7 introduce some resistance and thus voltage drop; this is compensated for in a manner discussed below).

When the circuit is to be operated in AC mode, DPDT switch 7, connected as shown, is controlled by the microprocessor, supplying a "POLARITY" signal, to alternate the polarity of the impedance being measured. That is, as compared to the method shown in the '663 patent, where an alternating polarity square wave was applied to the cell, and the output measured using full-wave rectification, according to this aspect of the present invention, the polarity of the cell is reversed, while the op-amps 1 see unchanged reference voltages $V_{Rp}$ and $V_{Rn}$. By switching the polarity of the cell instead of the polarity of the drive voltage, the output of the differential current-voltage converters is maintained at a nearly constant dc value, thereby minimizing the filtering required. When DC measurements are required, e.g., for measuring the resistance of a thermistor used to correct the conductivity measured with respect to a corresponding cell, switch 7 is simply left in the initial state; if only DC measurements are required, switch 7 can be eliminated altogether.

As noted, paired differential multiplexers 6 are responsive to a MUX signal from microprocessor 45 to select the impedance to be measured, $Z_1$ through $Z_n$. Several of these might be different conductivity cells, others thermistors provided for each conductivity cell, and the rest calibration resistances. For calibration purposes, one impedance should be open-circuit, allowing the measurement of current offset, i.e., the current measurement provided with no current flowing across the multiplexers 6. A second impedance should be a direct short for the similar measurement of voltage offset. (As will appear below, when the cell is shorted, the polarity switching and channel multiplexer analog switch resistances limit the current to a safe value). An additional impedance, comprising a temperature-stable calibration resistance, should be provided for near full scale calibration of each range.

The detailed operation of the circuit is best understood with reference to the simplified dc equivalent diagram of FIG. 7, which shows the case for either a DC measurement or a single half-cycle of an AC measurement. The analog switch resistances are each modeled as a simple resistance. As mentioned above, FIG. 7 also includes the dc equivalent circuit for the voltage-measuring circuit of FIG. 8, discussed below.

The voltage at the output of the upper current-voltage converter 1 is $$V_p = I_z R_f + V_{Rp}$$

where $V_{Rp}$ is a positive reference voltage, typically +0.5V; similarly, the voltage at the output of the lower converter 1 is $$V_n = V_{Rn} - I_z R_f$$

where $V_{Rn}$ is a negative reference voltage, typically −0.5V. The output of the differential instrumentation amplifier 11 is thus $$V_d = -G(2I_z R_f + (V_{Rp} - V_{Rn}))$$

where G is the voltage gain of amplifier 11. If we produce $V_{Rn}$ from $V_{Rp}$ by inverting the positive voltage reference, this becomes $$V_d = -2G(I_z R_f + V_{Rp})$$

and the output of the buffer 13 can be simply calculated as $$V_{I_z} = V_{Rp}\left[2G\frac{R_3}{R_2} - \frac{R_3}{R_1}\right] + 2GR_f\frac{R_3}{R_2}I_z$$

Now if the value of the offset resistor $R_1$ is adjusted to be $$R_1 = \frac{R_2}{2G}$$

the output of buffer 13 becomes simply $$V_{I_z} = 2GR_f\frac{R_3}{R_2}I_z$$

and the transimpedance gain is $$\frac{V_{I_z}}{I_z} = 2GR_f\frac{R_3}{R_2}$$

The offset introduced by the architecture of the differential current-voltage converter is thus substantially removed by using the same $V_{Rp}$ that produces the offset to compensate it. In operation, the microprocessor measures the output voltage $V_{iz}$ with an open-circuit channel selected and saves this value as the current offset. Clearly, this offset will also include circuit offsets generated by the amplifier input offsets and bias currents.

Again referring to FIG. 7, while the inverting inputs of the current-voltage converters are held at precisely $V_{Rp}$ and $V_{Rn}$, the voltage drops across $R_{polarity}$ and $R_{channel}$ (i.e., the voltage drops across the DPDT switch 7 and the multiplexers 6) are proportional to the current $I_z$ flowing through the switches and reduce the voltage applied across $Z_n$. Since the switch resistances vary widely and exhibit non-linear behavior, the voltage drop produced would cause significant measurement error if not compensated for. For this reason, a second circuit is required to accurately measure the voltage present across the impedance being measured.

ii. Voltage Measurement

Referring now to FIG. 8, the voltage sampling portion of the circuit is shown. This circuit is common to all embodiments of the circuit of the invention and serves to precisely measure the voltage across a selected cell impedance $Z_n$. A second differential channel multiplexer 18 (that is, comparable to but provided in addition to paired multiplexers 6 in FIG. 6) connects a further differential instrumentation amplifier 21, similarly buffered in a buffer amplifier 23, across the selected impedance $Z_n$ through a further polarity-controlling DPDT switch 19. In AC mode, the polarity switch 19 is driven with the same POLARITY control signal that drives the polarity inverting switch 7 in FIG. 6, and in this manner exactly compensates the inversion and again produces a nearly constant or DC value at the output of instrumentation amplifier 21.

Referring again to the simplified DC equivalent circuit of FIG. 7 for understanding of the detailed operation of the circuit of FIG. 8, it is apparent that input leakage current of amplifier 21 should be low to keep the voltage drop across the switch resistances low. The typical input bias current for an INA 121 amplifier from Burr-Brown is 4 pA and the switch resistance of a Maxim MAX337 multiplexer is 220 ohm, giving 220 ohm×10 pA=2.2 nV. For a voltage of 1 volt across the cell, this produces an error of only 2.2 nV/1V= 0.0022 ppm.

In this case the output voltage at the output of buffer 23 (neglecting R4 27 and the feedback capacitor 24 of FIG. 8) is simply $$V_{V_z} = G \frac{R_6}{R_5} V_{z_n}$$

Accordingly, the output of buffer 23 is directly proportional to the voltage across $Z_n$ with no offset. Of course, an offset will exist due to amplifier errors but these can be kept in the microvolt region by using chopper-stabilized amplifiers. With 1 volt across $Z_n$, an offset voltage of 10 represents only a 10 ppm error. If amplifiers with higher offsets are to be used, the offset can be measured by selecting a cell with zero impedance (shorted) and measuring the voltage Vvz.

iii. $C_p$ Compensation

As described in the '663 patent, the parallel capacitance $C_p$ of the conductivity cell (FIG. 5) is compensated for by switching the value of the feedback resistor 5 to a low or zero value during a short interval $t_c$ (~10 μs) at the start of each half-cycle, in this case, each time the polarity of the cell is switched with respect to the op amps 1. This is accomplished in the FIG. 6 circuit by controlling multiplexer 3 to select the zero ohm feedback element, i.e., conductor 5', during time $t_c$. During this charge time $t_c$ there will be a slight disturbance at the inverting input of the op-amp as it races to keep up with the current required to charge $C_p$ just after inversion. For this reason, it is beneficial to open the output multiplexer switches 4 by way of the ENABLE signal shown, and thus prevent this disturbance from affecting the output of amplifier 11. The capacitor 10 that forms part of the differential low-pass filter serves to stabilize the voltage during this brief interval when the output multiplexer 4 is open.

The required duration of $t_c$ can be simply calculated as follows: the charging current available is the maximum differential output voltage from amplifiers 1 divided by the sum of the series switch resistances. The time interval $t_c$ must be long enough to fully charge the maximum allowable $C_p$ to within the accuracy required.

With respect to the voltage sensing portion of the circuit shown in FIG. 8, the input to the output buffer 23 is switched to ground by switch 22 during the charge interval $\Delta t_c$, again to prevent the node disturbance from affecting the measured voltage. The capacitor 24 in the feedback loop of the output buffer filters the ripple thus produced.

iv. $C_x$ Compensation

Again as described in the '663 patent, $C_x$ errors are minimized by increasing the frequency with higher conductivity, i.e. by increasing the frequency of the POLARITY signal.

D. Integrating Version

Figure 9:
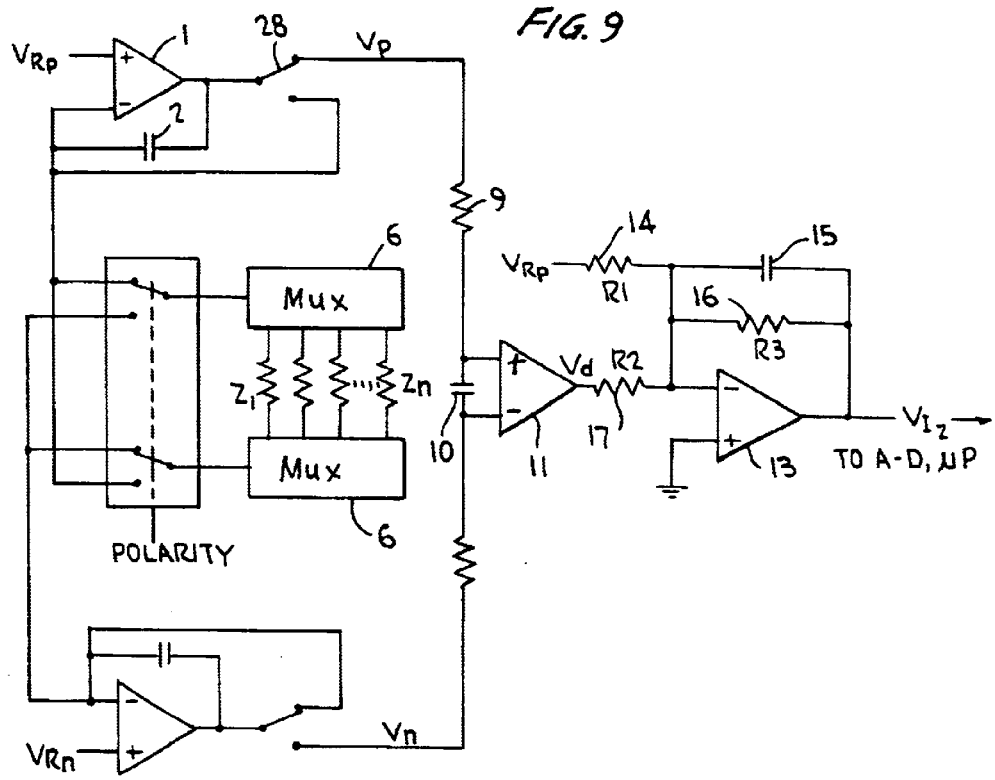
FIG. 9 is a schematic of the current-measuring portion of a variable-gain, integrating embodiment of the circuit.
Figure 10A:
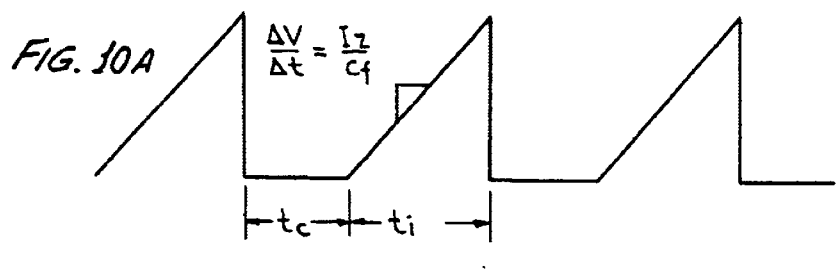
FIGS. 10(a) and (b) show waveforms encountered in operation of the circuit of FIG. 9.

As mentioned above, the current-measuring circuit of the invention can be implemented in a fixed-gain, resistive embodiment, as described in connection with FIG. 6, or an integrating embodiment, which is shown in FIG. 9. As will be apparent from comparing FIGS. 6 and 9, both embodiments of the circuit include numerous common components, and operate similarly, particularly with respect to the polarity inversion of the cell (or other impedance to be measured), as provided by polarity-switching DPDT switch 7, paired multiplexers 6, which allow measurement of the impedance of several cells' conductivity and resistance, as well as open and short circuits, used to establish voltage and current offset values respectively, and the output circuit, comprising the instrumentation amplifier 11, buffer 13, and their associated circuitry. The main difference between the fixed-gain resistive circuit of FIG. 6 and the integrating circuit of FIG. 9 is that in the latter, the several feedback resistors and range multiplexers of the former (that is, as provided on both symmetrical sides of the complete circuit) are each replaced with a single feedback capacitor 2 and a SPDT switch 28. Referring to a single side of the circuit, during $t_c$, the switch 28 shorts out the feedback capacitor 2 and charges $C_p$. At the end of $t_c$, the switch 28 is switched to the position shown in FIG. 9, and capacitor 2 begins charging at a rate proportional to the cell current. See FIG. 10(a), showing the voltage across the upper capacitor 2 as a function of time. Several cycles are shown; as noted, their duration is controlled by the switching of the polarity switch 7, and is controlled in accordance with the desired conductivity range. As illustrated, during $t_c$ the voltage remains at zero; at the end of $t_c$, i.e., when switches 28 are operated, the voltage across the capacitor 2 begins to ramp up at a rate proportional to the cell current, and thus to its resistance. The remainder of the cycle is the integration time $t_i$.

Figure 10B:
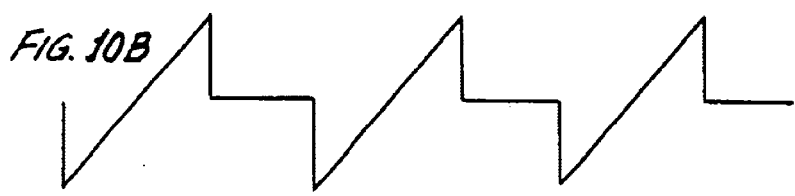

A differential first-order filter comprising resistors 9 and capacitor 10, with a time constant much larger than the drive period, extracts the average from the waveform shown. Because the resistors 9 are floating during $t_c$, the signal at $V_p$-$V_n$, i.e., the switched output of the op-amps 1, appears as shown in FIG. 10(b).

The average output of the differential instrumentation amplifier 11 is $$V_d = -G\left[\frac{I_z}{C_f}\Delta t_i + (V_{Rp} - V_{Rn})\right] \quad \text{where} \quad \Delta t_i = \frac{T}{2} - \Delta t_c$$

with T=drive frequency and $\Delta t_c$= the $C_p$ charge interval. The equation for the output of the buffer 13 is $$V_{I_z} = V_{Rp}\left[2G\frac{R_3}{R_2} - \frac{R_3}{R_1}\right] + G\frac{R_3}{R_2}\frac{I_z}{C_f}\Delta t_i$$

As before, if we adjust the value of the offset resistor $R_1$ to be $$R_1 = \frac{R_2}{2G}$$

the output becomes simply $$V_{I_z} = G\frac{R_3}{R_2}\frac{I_z}{C_f}\Delta t_i$$

and the transimpedance gain is $$\frac{V_{I_z}}{I_z} = \frac{G}{C_f}\frac{R_3}{R_2}\Delta t_i$$

We see that the gain of the circuit is proportional to the time allowed for integration, or in terms of drive frequency, $$\frac{V_{I_z}}{I_z} = \frac{G}{C_f}\frac{R_3}{R_2}\left[\frac{1}{2f_d} - \Delta t_c\right]$$

There are several distinct advantages to the integrating approach, as follows:

First, the range-selecting resistors 5 and selection multiplexers 3 and 4 are eliminated, reducing the parts count and product cost, as well as eliminating these as sources of errors.

Second, the range of the instrument can be selected continuously by simply varying the drive frequency. Instead of, for example, three fixed ranges, any range can be selected at any time.

Third, the integrating gain stage provides the most first-order filtering possible in the first stage. This level of filtering, combined with the post filtering of the sigma-delta converter, yields close to 24 bit performance with the lamp on (i.e., under extremely noisy conditions).

Fourth, increasing the drive frequency (i.e., the frequency of polarity reversal) with increasing conductance keeps the $C_x$ error constant. As disclosed in the '663 patent, the error due to $C_x$ results from $C_x$ charging through the cell resistance and reducing the voltage across the same resistance. The longer the period of time it is allowed to charge the larger this error becomes. In order to keep the error below a specified limit as the conductance is increased, the drive frequency must be correspondingly increased. The integrating version does just this, and in a continuous fashion.

E. Filtering and Sigma-Delta Converters

In the resistive embodiment of the circuit of the invention (FIG. 6), the feedback capacitor 2 should be small in order to maximize signal response. After each charge pulse, at which time capacitor 2 is discharged, the output will rise with a time constant τ=RC, and this should be short relative to the half-cycle width. If, in an effort to increase noise rejection, additional capacitors are put across the feedback resistors, a substantial non-linearity will be generated due to disturbances resulting from the capacitive coupling between the output and the node.

The integrating embodiment of the circuit of the invention (FIG. 9), on the other hand, uses as much capacitance as possible in the feedback loop and therefore achieves the most first order filtering possible at this first stage. More important, however, is how the integrating version maintains tight control over the transients at the inverting input during the transition from the $C_x$ charge period $t_c$ to the integration interval $t_i$.

Figure 11:
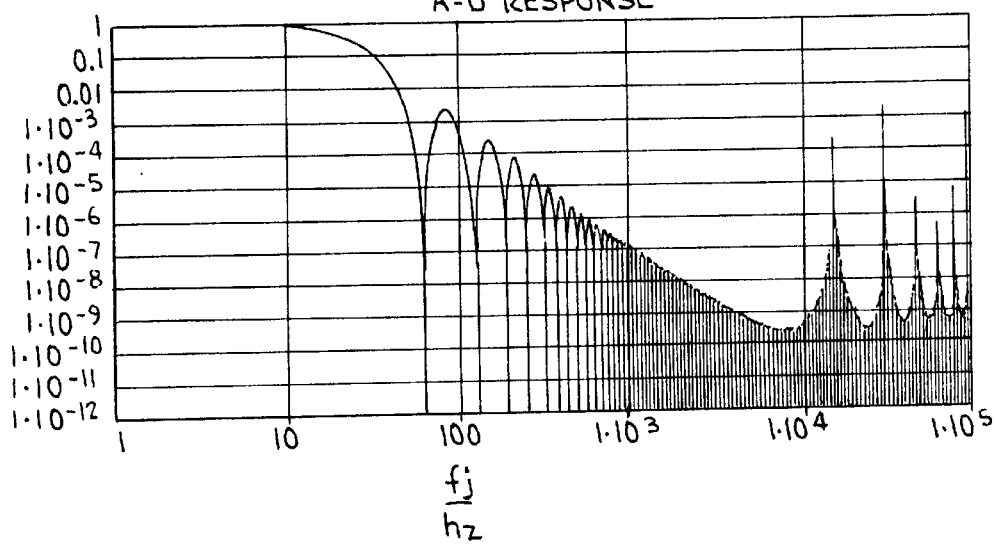
FIGS. 11–14 are graphs illustrative of the response of the circuit, as preferably implemented.
Figure 12:
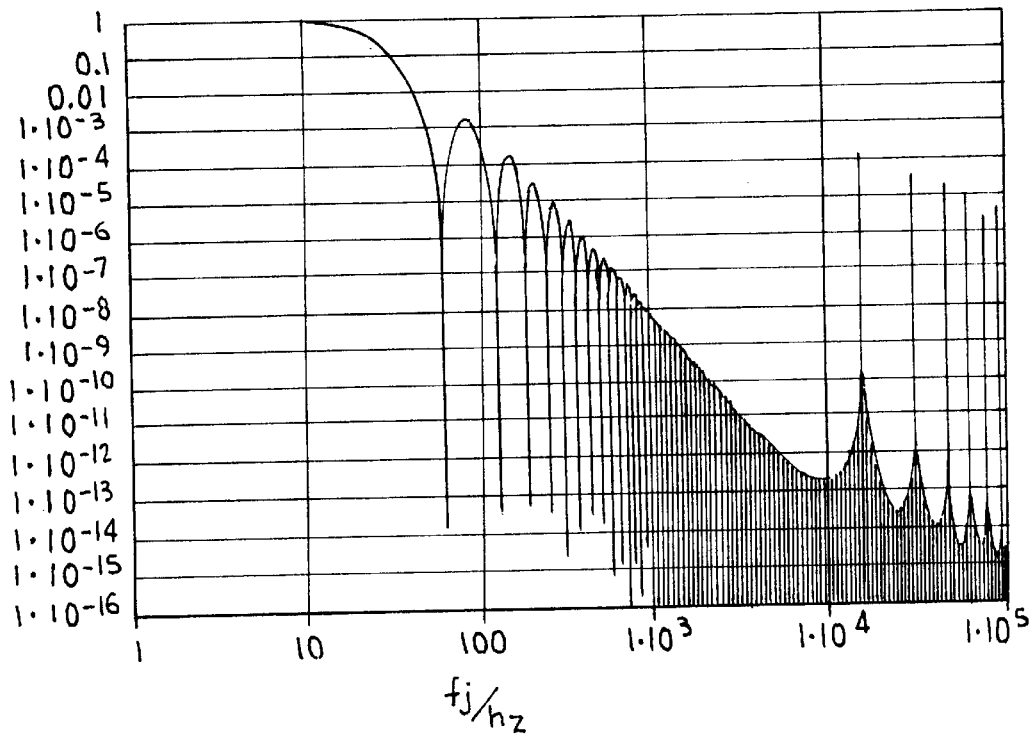

Sigma-delta converters use a single-bit, oversampled A-D conversion technique. Then the resulting bitstream is digitally averaged, within the A-D chip itself, to produce the reading. In this context, the A-D filter is used to convert the analog voltages produced by the circuits of FIGS. 6–9 to digital values, which are then used by the microprocessor 45 to determine the actual temperature-corrected TOC values of interest. In the preferred embodiment, the LTC2400 from Linear Technology, an inexpensive 24 bit A-D converter that uses a $4^{th}$ order digital post filter, is employed. The filter, basically a commutating filter, passes narrow frequency bands at the sampling frequency and harmonics thereof. The frequency response of this converter, sampling at 15 khz, is shown in FIG. 11, which depicts the transfer function, i.e., gain, of the filter on the vertical axis versus signal frequency on the horizontal axis. The spikes in the frequency response indicate a gain of 1 at the 15 khz sampling frequency and integral multiples thereof Accordingly, if the lamp frequency (or some component thereof) happens to be at the sampling frequency (15 khz) it will pass through with a gain of 1, greatly interfering with accurate measurements. It is therefore necessary to add prefiltering, also known as anti-aliasing filters, to reduce the response at these narrow frequency bands to acceptable levels. In the resistive embodiment of the circuit of the invention (FIG. 6), the differential filter with R 9=10 k ohm and C 10=0.047 µf, and the buffer filter, R3 16=100 k ohm and C 15=0.01 µf, together provide two poles of prefiltering, resulting in the overall response shown in FIG. 12. As can be seen, the spikes at 15 khz and multiples thereof are substantially attenuated, reducing the effects of lamp noise.

Figure 13:
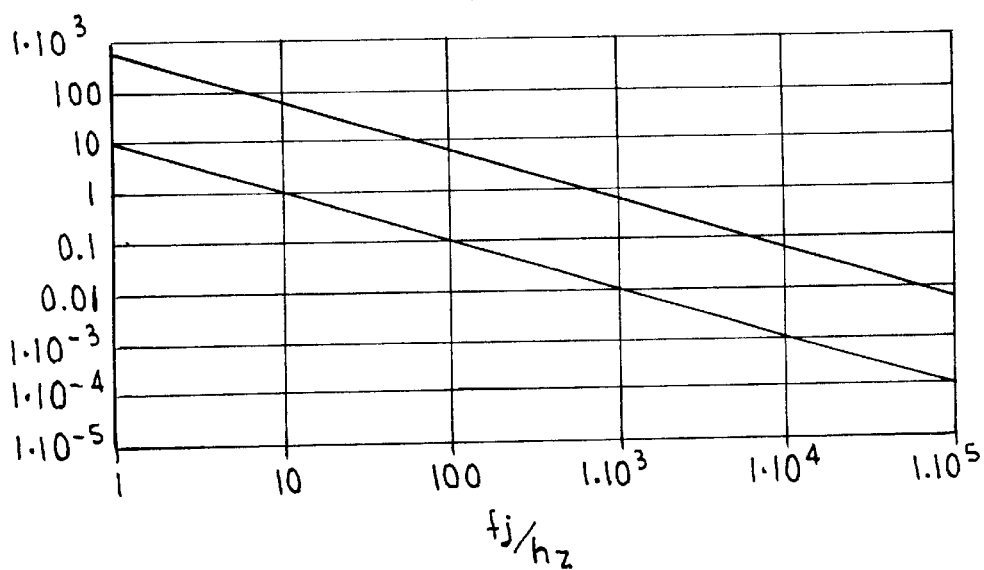
Figure 14:
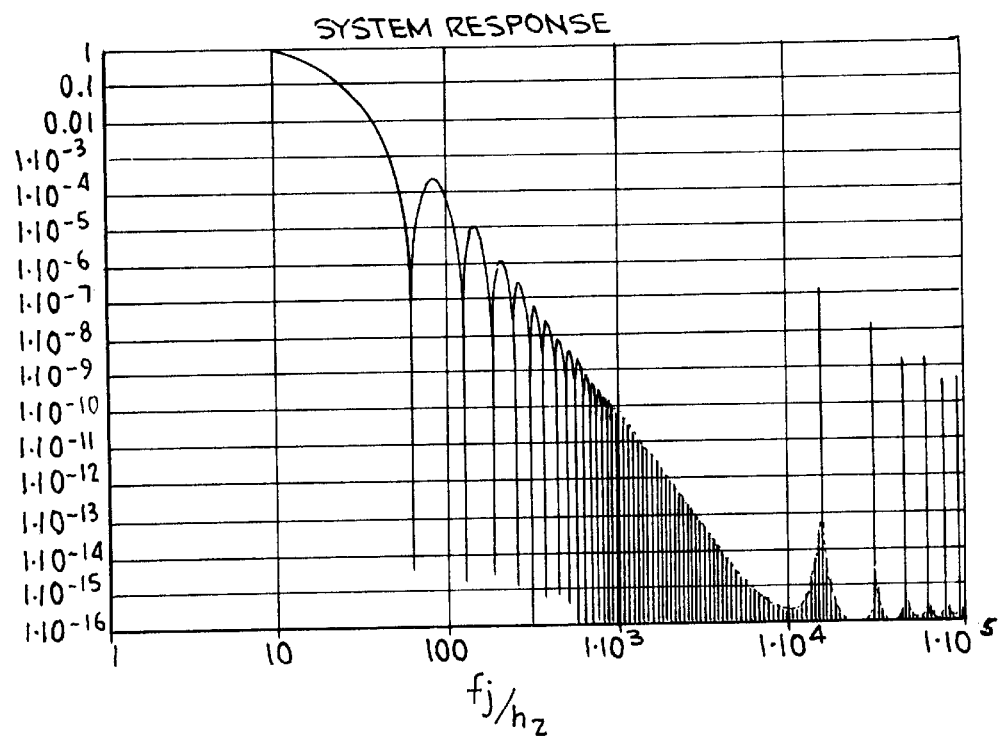

With the integrating version, the integrator response crosses 0 db (gain=1) at a frequency that is inversely proportional to the cell resistance, i.e., as the cell resistance goes up, the 0 db frequency goes down. See FIG. 13, in which the top trace is with a cell resistance of 100 k ohms and the lower trace with a cell resistance of 6 Mohm (equivalent to pure water with the cell design discussed above). This is ideal with respect to filtering, because the higher the cell resistance the more noise and the more filtering needed. The overall system response with a cell resistance of 6 Mohm is shown in FIG. 14. As illustrated, an exceptional amount of filtering is provided, with even the leakage at the sampling frequency down by a factor of nearly $10^7$. It is for this reason that the instrument of the invention provides nearly 24 bit repeatability of measurements, even when the very noisy lamp that is used to drive rapid oxidation is activated.

3. Sample Dilution for Range Broadening

The instrument described above is designed to analyze the TOC of reclaim/recycle water systems as typically used throughout semiconductor manufacturing plants. As such, the instrument is designed to accurately measure up to 2000 ppb TOC in waters with up to 10 µS/cm conductivity, which are typical outer limits for water to be acceptable. However, in some cases the recycled water initially has more TOC or has higher conductivity than the instrument can analyze. Since semiconductor plants typically have a supply of ultrapure water (UPW) available, the recycled water stream could be diluted with a stream of UPW to dilute the TOC and/or conductivity to fall within the useful range of the instrument.

Figure 15:
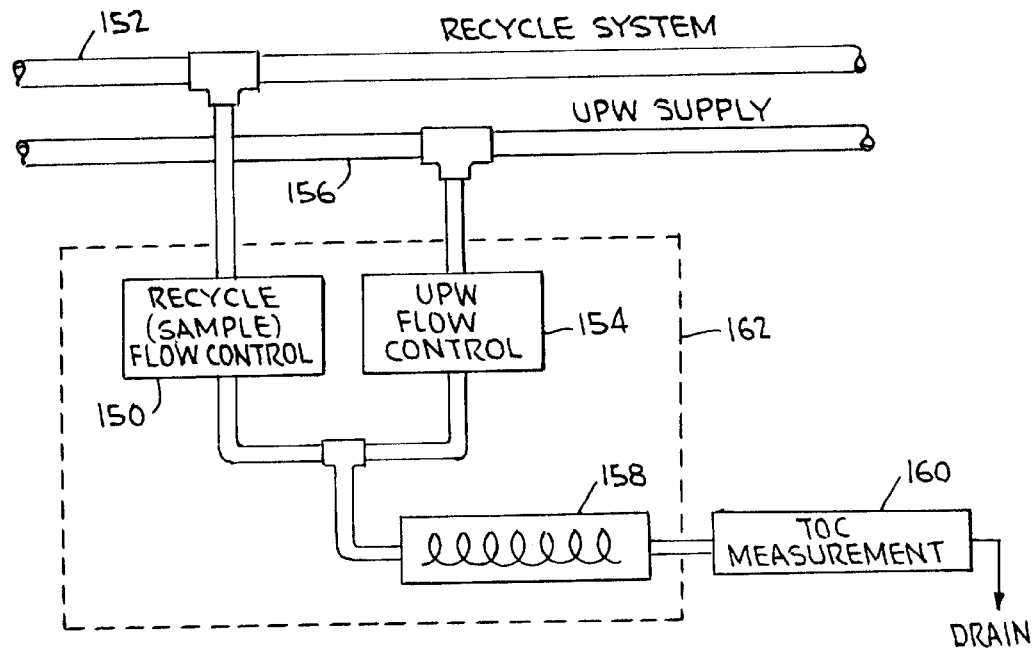
FIG. 15 illustrates the principle of operation of the instrument in a further embodiment comprising means for diluting samples insufficiently resistive, or containing excessive TOC, to permit accurate measurement of their TOC.

In order to accomplish an analytical on-line dilution, that is, in order to dilute the TOC or conductivity of the recycle/reclaim stream without rendering the measurement inaccurate, it is necessary to accurately control and measure the flow rate of the sample stream and the flow rate of the diluent stream. One way to achieve a known flow rate is by using a pair of highly accurate pumps, such as peristaltic or syringe pumps, one pump for the diluent and one pump for the sample stream. See FIG. 15, illustrating a typical arrangement. A first pump 150 is connected to draw a controlled amount of the recycle/reclaim water to be monitored for TOC contents from a line 152, while a second pump 154 similar draws the diluting UPW from a second line 156. The pumps 150, 154 are each set independently for a desired flow rate depending on the required dilution. The sample and diluent streams would then be thoroughly mixed in a mixer 158, typically comprising a flow passage of complicated shape, as indicated, to ensure thorough mixing, and supplied to the TOC measurement instrument 160, as shown.

Alternatively, the flow rate (of the sample stream, the diluent, or both) could be controlled by using a pressure-control system similar to the analytical flow system in the continuous flow part of the TOC instrument itself, e.g., as described in connection with FIG. 3 above. First the pressure is coarsely adjusted with a metering valve and a check valve with an appropriate cracking pressure. Next the flow is directed to a differential pressure sensor with a reference pressure. The flow is then sent to a tee with a first precision orifice on one side of the tee. The final flowrate is determined by the diameter of the precision orifice. Finally the controlled flow is directed to a set of pressure transducers in series separated by a second precision orifice. The flowrate is controlled by the coarse and fine pressure control combined with the first precision orifice, and measured by measuring the pressure drop across the second precision orifice. The diameter of the first precision orifice is determined by the required flowrate. The diameter of the second precision orifice is determined by the range of pressures, i.e., its diameter as compared to that of the first precision orifice sets the relative pressures of the sample and diluent flow. Both the sample stream and the diluent stream would have this scheme implemented. Typically, one or both streams would have their flow rate made adjustable, by using a micrometer-adjustable first metering orifice. Again, the final dilution is a ratio of the diluent flow rate to the sample flow rate times the TOC concentration or the conductivity.

Another possibility for providing precise control of the sample and diluent flow rates, and thus of the dilution ratio, would be to use two liquid mass-flow controllers, one on each stream, or to use such a mass-flow controller on one stream and a constant flow rate controller (again, either a precision pump or a combination of pressure control and a precision orifice) on the other.

The equipment required to accomplish this carefully controlled dilution, whether comprised of pumps or pressure control, would typically be configured as a secondary module 162, connected between the sample and UPW supplies 152, 156 on one side and the TOC instrument 160 on the other, as illustrated.

The advantage of the pumping system is that it is independent of the system pressure. The disadvantage is the expense of two precision pumps, and their regular maintenance. The advantage of the pressure control system is reduced maintenance and lower cost; the corresponding disadvantage is the requirement that the pressures of the sample stream and the diluent stream must fall between compatible minimum and maximum values.

In either case, the diluted sample concentration is a ratio of the sample flow rate to the diluent flow rate times the sample TOC concentration or conductivity. For example, if the conductivity is 100 $\mu$S/cm and the TOC is 1000 ppb, setting the sample flowrate to 5 mL/min and the diluent flowrate to 100 mL/min will produce a diluted sample flow of 105 mL/min to the instrument with a conductivity of approximately 5 $\mu$S/cm and a TOC concentration of 50 ppb, as follows:

{(5 mL/min)/100 mL/min)*1000 ppb}=50 ppb TOC

{(5 mL/min)/100 mL/min)*100 $\mu$S/cm}=5 $\mu$S/cm

In some cases, especially when the source of the conductivity is a weak acid, the dilution of the sample stream will not produce a linear dilution of the conductivity. The diluted conductivity will be higher than predicted by linear dilution. In this case further dilution, with a greater ratio of sample flow to diluent flow is required to bring the diluted conductivity to within the range of the instrument. However, TOC in the sample will vary linearly with the dilution ratio, so that the sample TOC can be determined by multiplying the measured TOC by the dilution ratio.

The advantage of this dilution system is that it can increase the dynamic range of the on-line instrument. The disadvantages are that it requires a steady source of diluent water and that it is possible, under water conditions where the TOC is low and the conductivity high, to dilute the sample to below the detection limits of the instrument. Attached is a table that compares the useful operating range of the instrument of the invention in sample waters, taking into account the nominal range of the instrument and the expected range of conductivities of the semiconductor reclaim/recycle water.

This on-line dilution scheme is applicable to any on-line analytical measurement when the sample concentration of the species to be measured, or the concentration of an interfering species, is greater than the capabilities of the analytical instrument.

Dilution Table
Conductivity $\mu$S/cm

|  |  | 20 | 50 | 100 | 125 | 150 | 200 |
|---|---|---|---|---|---|---|---|
| TOC (ppbC) | 100 | 1:10 2(10) | N/A (2(4)) | N/A (2(2)) | N/A (2(1.6)) | N/A (2(1.3)) | N/A (2(1) |
|  | 500 | 1:10 2(50) | 1:25 2(20) | 1:50 2(10) | N/A (2(8)) | N/A (2(6.7)) | N/A (2(5) |
|  | 1000 | 1:10 2(100) | 1:25 2(40) | 1:50 2(20) | 1:62.5 2(16) | 1:75 2(13) | 1:100 2(10 |
|  | 5000 | 1:20 1(100) | 1:50 1(100) | 1:100 1(50) | 1:62.5 2(80) | 1:75 2(67) | 1:100 2(50 |
|  | 10000 | 1:20 1(500) | 1:50 1(200) | 1:100 1(100) | 1:125 1(80) | 1:150 1(67) | 1:200 1(50 |
|  | 25000 | 1:20 1(125) | 1:50 1(500) | 1:100 1(250) | 1:125 1(200) | 1:150 1(168) | 1:200 1(12 |

X:XXX = Dilution ratio
(X(XX)) = (Cond. after dilution(TOC after dilution))
Assumptions for concentrations after dilution:
Minimum TOC = 10 ppbC
Maximum Cond = 2 $\mu$S/cm

Having now disclosed the invention in detail, several important advantages thus provided can be summarized as follows:

1) Combing both continuous-flow and static sample TOC measurement capability in a single instrument allows accurate, yet substantially instantaneous TOC values to be provided.

2) Providing a full differential conductivity measurement allows essentially complete noise rejection, allowing use of a powerful UV lamp for rapid oxidation, while optimizing the circuit for use with sigma-delta A-D converters allows 24-bit accuracy.

3) Providing controlled dilution of the sample stream broadens the range of the instrument with respect to both the range of TOC that can be measured and the conductivity of the water itself.

While a preferred embodiment of the invention and several alternatives thereto have been discussed in detail, those of skill in the art will recognize that numerous further alternatives and equivalents are within the skill of the art. Accordingly, the invention should not be limited thereby, but only by the following claims.

What is claimed is:

1. A circuit for measuring the conductivity of an aqueous sample, comprising:

a cell for containing said sample;

a pair of electrodes in said cell;

first and second operational amplifiers, each being provided with an oppositely-polarized stable voltage reference connected to its noninverting input and being connected in a feedback loop, each of said electrodes being connected to the inverting input of one of said operational amplifiers, whereby the output of each operational amplifier is a voltage signal responsive to the current flowing through said cell, but the signs of their respective output voltages are opposite;

an instrumentation amplifier responsive to the difference in the oppositely-polarized output voltage signals of said operational amplifiers; and means for converting an output voltage signal provided by said instrumentation amplifier responsive to the difference in the oppositely-polarized output voltage signals of said operational amplifiers into a value for the conductivity of said aqueous sample.

2. The circuit of claim 1, further comprising switch means for controlling the polarity whereby said electrodes are connected to said operational amplifiers.

3. The circuit of claim 2, further comprising means for controlling the frequency of switching of said polarity responsive to the approximate conductivity of said sample, to reduce errors caused by a capacitance $C_x$ in series with the conductivity of said sample in said cell to be measured.

4. The circuit of claim 3, wherein said circuit is implemented in an instrument controlled by a microprocessor, and wherein said microprocessor controls the frequency of switching of said polarity.

5. The circuit of claim 1, further comprising multiplexer means for connecting plural conductivity cells, and/or other components the conductivity or another electrical characteristic of which are to be measured, across said operational amplifiers.

6. The circuit of claim 1, further comprising a further instrumentation amplifier connected to provide an output voltage signal proportional to the voltage across said conductivity cell.

7. The circuit of claim 1, further comprising a set of fixed resistances connected by controllable multiplexer means in the feedback loop of each of first and second operational amplifiers for setting the rate of charging of a capacitance $C_p$ effectively in parallel with the conductivity to be measured of said sample in said cell.

8. The circuit of claim 7, wherein said circuit is implemented in an instrument controlled by a microprocessor, and wherein said microprocessor controls the selection of said fixed resistance from said set of fixed resistances.

9. The circuit of claim 1, wherein said feedback loops comprise a fixed capacitance and no resistance, whereby the voltage signal provided by each of said operational amplifiers is an integrated signal.

10. The circuit of claim 1, wherein the output signal from said instrumentation amplifier is supplied to a buffer amplifier with a feedback capacitor, to add an additional pole of filtering.

11. The circuit of claim 10, wherein the output signal from said buffer amplifier is supplied to an analog-to-digital converter including internal filtering.

12. The circuit of claim 11, wherein said analog-to-digital converter is a sigma-delta converter.

13. A method for measuring the conductivity of an aqueous sample, comprising the steps of:

disposing said sample in a cell containing a pair of electrodes;

connecting said electrodes to the inverting inputs of first and second operational amplifiers;

connecting the noninverting inputs of said operational amplifiers to oppositely-polarized stable voltage references, and connecting the inverting inputs of each of said operational amplifiers in a feedback loop, whereby the output of each operational amplifier is a voltage signal responsive to the current flowing through said sample, but the signs of their respective output voltage signals are opposite;

connecting the oppositely-polarized output voltage signals of said operational amplifiers to an instrumentation amplifier providing a output voltage signal responsive to the difference; and converting said output voltage signal provided by said instrumentation amplifier into a value for the conductivity of said aqueous sample.

14. The method of claim 13, comprising the further step of periodically reversing the polarity whereby said electrodes are connected to said operational amplifiers.

15. The method of claim 14, comprising the further step of controlling the frequency of switching of said polarity responsive to the approximate conductivity of said sample, to reduce errors caused by a capacitance $C_x$ in series with the conductivity of said sample in said cell to be measured.

16. The method of claim 15, wherein said circuit is implemented in an instrument controlled by a microprocessor, and comprising the further step of employing said microprocessor to control the frequency of switching of said polarity.

17. The method of claim 13, comprising the further step of employing multiplexer means for connecting plural conductivity cells, and/or other components the conductivity or another electrical characteristic of which are to be measured, across said operational amplifiers.

18. The method of claim 13, comprising the further steps of providing a further instrumentation amplifier connected to provide an output voltage signal proportional to the voltage across said conductivity cell, and using said signal and the voltage signal proportional to the current through said cell to determine the conductivity thereof.

19. The method of claim 13, comprising the further steps of providing a set of fixed resistances connected by controllable multiplexer means in the feedback loop of each of first and second operational amplifiers, and selecting one of said fixed resistances for setting the rate of charging of a capacitance $C_p$ effectively in parallel with the conductivity to be measured of said sample in said cell.

20. The method of claim 19, wherein said circuit is implemented in an instrument controlled by a microprocessor, and wherein said microprocessor controls the selection of said fixed resistance from said set of fixed resistances.

21. The method of claim 13, wherein said feedback loops each comprise a fixed capacitance and no resistance, whereby the voltage signal provided by each of said operational amplifiers is integrated by said capacitor.

22. The method of claim 13, wherein the output signal from said instrumentation amplifier is supplied to a buffer amplifier with a feedback capacitor to add an additional pole of filtering.

23. The method of claim 22, wherein the output signal from said buffer amplifier is supplied to an analog-to-digital converter including internal filtering.

24. The method of claim 23, wherein said analog-to-digital converter is a sigma-delta converter.

* * * * *